(12) United States Patent
Fang et al.

(10) Patent No.: US 7,211,590 B2
(45) Date of Patent: May 1, 2007

(54) NITROSATED PROTON PUMP INHIBITORS, COMPOSITIONS AND METHODS OF USE

(75) Inventors: Xinqin Fang, Lexington, MA (US); David S. Garvey, Dover, MA (US); L. Gordon Letts, Dover, MA (US)

(73) Assignee: NitroMed, Inc., Lexington, MA (US)

( * ) Notice: Subject to any disclaimer, the term of this patent is extended or adjusted under 35 U.S.C. 154(b) by 281 days.

(21) Appl. No.: 10/631,782

(22) Filed: Aug. 1, 2003

(65) Prior Publication Data
US 2004/0024014 A1    Feb. 5, 2004

Related U.S. Application Data

(60) Provisional application No. 60/399,715, filed on Aug. 1, 2002.

(51) Int. Cl.
C07D 401/04    (2006.01)
A61K 31/44     (2006.01)

(52) U.S. Cl. .................................. 514/338; 546/273.7

(58) Field of Classification Search ................ 514/338; 546/273.7
See application file for complete search history.

(56) References Cited

U.S. PATENT DOCUMENTS

| | | |
|---|---|---|
| 4,045,563 A | 8/1977 | Berntsson et al. |
| 4,255,431 A | 3/1981 | Junggren et al. |
| 4,337,257 A | 6/1982 | Junggren et al. |
| 4,359,465 A | 11/1982 | Ruwart |
| 4,628,098 A | 12/1986 | Nohara et al. |
| 4,634,710 A | 1/1987 | Fischli et al. |
| 4,758,579 A | 7/1988 | Kohl et al. |
| 4,806,549 A | 2/1989 | Ife et al. |
| 4,806,550 A | 2/1989 | Ife et al. |
| 4,808,596 A | 2/1989 | Matsuishi et al. |
| 4,818,760 A | 4/1989 | Binder et al. |
| 4,839,365 A | 6/1989 | Hirai et al. |
| 4,845,118 A | 7/1989 | Lang et al. |
| 4,871,734 A | 10/1989 | Lang et al. |
| 4,873,337 A | 10/1989 | Sih et al. |
| 4,956,366 A | 9/1990 | Nimmesgern et al. |
| 4,981,861 A | 1/1991 | Fischli et al. |
| 5,045,552 A | 9/1991 | Souda et al. |
| 5,114,955 A | 5/1992 | Lang et al. |
| 5,149,702 A | 9/1992 | Yamada et al. |
| 5,380,758 A | 1/1995 | Stamler et al. |
| 5,391,752 A | 2/1995 | Hoerrner et al. |
| 5,403,830 A | 4/1995 | Place |
| 5,439,917 A | 8/1995 | Briving et al. |
| 5,470,983 A | 11/1995 | Slemon et al. |
| 5,554,631 A | 9/1996 | Kim et al. |
| 5,599,794 A | 2/1997 | Eek et al. |
| 5,610,178 A | 3/1997 | Zeeck et al. |
| 5,629,305 A | 5/1997 | Eek et al. |
| 5,631,293 A | 5/1997 | Kleemann et al. |
| 5,641,792 A | 6/1997 | Kleemann et al. |
| 5,665,730 A | 9/1997 | Senn-Bilfinger et al. |
| 5,677,302 A | 10/1997 | Karimian et al. |
| 5,686,458 A | 11/1997 | Lee et al. |
| 5,703,073 A | 12/1997 | Garvey et al. |
| 5,703,097 A | 12/1997 | Kim et al. |
| 5,714,504 A | 2/1998 | Lindberg et al. |
| 5,750,531 A | 5/1998 | Lee et al. |
| 5,945,425 A | 8/1999 | Moormann et al. |
| 5,952,504 A | 9/1999 | Yoo et al. |
| 5,990,311 A | 11/1999 | Hong et al. |
| 6,323,234 B1 | 11/2001 | Garvey et al. |
| 6,365,184 B1 | 4/2002 | Depui et al. |

(Continued)

FOREIGN PATENT DOCUMENTS

DE        44 20 523       12/1995

(Continued)

OTHER PUBLICATIONS

Sih et al. 1991. *J. Med. Chem.* 34, 1049-1062.

(Continued)

*Primary Examiner*—D. Margaret Seaman
(74) *Attorney, Agent, or Firm*—Wilmer Cutler Pickering Hale and Dorr LLP

(57) ABSTRACT

The invention describes novel nitrosated proton pump inhibitor compounds and pharmaceutically acceptable salts thereof, and novel compositions comprising at least one nitrosated proton pump inhibitor compound, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one nitrosated proton pump inhibitor compound, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one nitrosated proton pump inhibitor compound, and, optionally, at least one nitric oxide donor and/or at least one therapeutic agent. The invention also provides methods for treating gastrointestinal disorders; facilitating ulcer healing; decreasing the recurrence of ulcers; improving gastroprotective properties, anti-*Helicobacter pylori* properties or antacid properties of proton pump inhibitors; decreasing or reducing the gastrointestinal toxicity associated with the use of nonsteroidal antiinflammatory compounds; treating bacterial infections and/or viral infections.

24 Claims, No Drawings

U.S. PATENT DOCUMENTS

| | | | |
|---|---|---|---|
| 6,436,975 B1 | 8/2002 | Del Soldato | |
| 6,503,929 B1 | 1/2003 | Del Soldato | |
| 6,613,354 B2 | 9/2003 | Depui et al. | |
| 6,673,819 B2 * | 1/2004 | Bergman et al. | 514/338 |
| 6,852,739 B1 * | 2/2005 | Garvey et al. | 514/338 |
| 6,897,227 B2 | 5/2005 | Garst et al. | |
| 6,906,078 B2 | 6/2005 | Moorman et al. | |
| 2001/0047038 A1 | 11/2001 | Moorman et al. | |
| 2002/0111370 A1 | 8/2002 | Bergman et al. | |
| 2002/0155153 A1 | 10/2002 | Depui et al. | |
| 2003/0027844 A1 | 2/2003 | Del Soldato | |
| 2003/0161846 A1 | 8/2003 | Holmberg et al. | |
| 2004/0022846 A1 | 2/2004 | Depui et al. | |
| 2004/0082605 A1 | 4/2004 | Eek | |
| 2004/0102484 A1 | 5/2004 | Garst et al. | |
| 2005/0042282 A1 | 2/2005 | Ieni | |

FOREIGN PATENT DOCUMENTS

| | | |
|---|---|---|
| EP | 0033094 | 8/1981 |
| EP | 0045200 | 2/1982 |
| EP | 0221041 | 5/1987 |
| EP | 0234485 | 9/1987 |
| EP | 0246774 | 11/1987 |
| EP | 0254588 | 1/1988 |
| EP | 0259174 | 3/1988 |
| EP | 1352660 | 10/2003 |
| JP | 11-171791 | 6/1999 |
| WO | 89/08104 | 9/1989 |
| WO | 92/12969 | 8/1992 |
| WO | 95/27714 | 10/1995 |
| WO | 96/24375 | 8/1996 |
| WO | WO 97/02021 | 1/1997 |
| WO | 97/25054 | 7/1997 |
| WO | 97/25064 | 7/1997 |
| WO | 97/32854 | 9/1997 |
| WO | 98/18784 | 5/1998 |
| WO | WO 98/22118 | 5/1998 |
| WO | 98/43968 | 10/1998 |
| WO | 98/54172 | 12/1998 |
| WO | 98/57626 | 12/1998 |
| WO | 99/44595 | 9/1999 |
| WO | 99/45004 | 9/1999 |
| WO | 00/12064 | 3/2000 |
| WO | 00/50038 | 8/2000 |
| WO | WO 00/50037 | 8/2000 |
| WO | WO 00/61537 | 10/2000 |
| WO | WO 00/61541 | 10/2000 |
| WO | 00/69438 | 11/2000 |
| WO | 00/72838 | 12/2000 |
| WO | WO 01/12584 | 2/2001 |
| WO | 01/44257 | 6/2001 |
| WO | 01/66088 | 9/2001 |
| WO | 01/85167 | 11/2001 |
| WO | 02/00166 | 1/2002 |
| WO | WO 02/00166 A2 * | 1/2002 |
| WO | WO 02/051385 | 7/2002 |
| WO | 02/069968 | 9/2002 |
| WO | 03/022249 | 3/2003 |
| WO | 03/022269 | 3/2003 |
| WO | 03/053221 | 7/2003 |
| WO | 03/080029 | 10/2003 |
| WO | WO 03/097011 | 11/2003 |

OTHER PUBLICATIONS

Wallace et al. 1994. *Journal of Gastroenterology and Hepatology.* 9, S40-S44.

Barrachina et al. 1995. *European Journal of Pharmacology.* 281, R3-R4.

Brunton et al. 1996. *The Pharmacological Basis of Therapeutics.* 9th Edition. pp. 901-915.

Supplementary European Search Report for EP Application No. 03 76 7016 dated Aug. 4, 2006.

* cited by examiner

NITROSATED PROTON PUMP INHIBITORS, COMPOSITIONS AND METHODS OF USE

RELATED APPLICATIONS

This application claims priority under 35 USC § 119 to U.S. application Ser. No. 60/399,715 filed Aug. 1, 2002.

FIELD OF THE INVENTION

The invention describes novel nitrosated proton pump inhibitor compounds and pharmaceutically acceptable salts thereof, and novel compositions comprising at least one nitrosated proton pump inhibitor compound, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one nitrosated proton pump inhibitor compound, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one nitrosated proton pump inhibitor compound, and, optionally, at least one nitric oxide donor and/or at least one therapeutic agent. The invention also provides methods for treating gastrointestinal disorders; facilitating ulcer healing; decreasing the recurrence of ulcers; improving gastroprotective properties, anti-*Helicobacter pylori* properties or antacid properties of proton pump inhibitors; decreasing or reducing the gastrointestinal toxicity associated with the use of nonsteroidal antiinflammatory compounds; treating bacterial infections and/or viral infections.

BACKGROUND OF THE INVENTION

The proton pump, located in the apical membrane of the parietal cell, is responsible for the secretion of acid in the stomach when it is stimulated by the enzyme adenosine triphosphate ($H^+$, $K^+$)-ATPase. Proton pump inhibitors are a class of anti-secretory compounds used in the management of gastrointestinal disorders. They suppress gastric acid secretion by the specific inhibition of the ($H^+$, $K^+$)-ATPase enzyme system at the secretory surface of the gastric parietal cell.

A family of substituted benzimidazoles have been developed as specific proton pump inhibitors. Two of these compounds, omeprazole and lansoprazole, are used clinically in the United States. Structurally they contain a sulfinyl group bridging between substituted benzimidazole and pyridine rings. At a neutral pH, omeprazole and lansoprazole are chemically stable, are weak bases, are lipid-soluble, and do not show any inhibitory activity. Once these compounds reach the parietal cells and diffuse into the secretory canaliculi, they become protonated. The protonated compounds rearrange to form sulfenic acid and then a sulfenamide. The latter interacts covalently with sulfhydryl groups at critical sites in the extracellular (luminal) domain of the membrane spanning ($H^+$, $K^+$)-ATPase. Inhibition occurs when two molecules of the inhibitor are bound per molecule of the enzyme. The specificity of these proton pump inhibitors arises from the selective distribution of the ($H^+$, $K^+$)-ATPase, the acid-catalyzed rearrangement of the compounds to generate the active inhibitor, and the trapping of the protonated compound and the cationic sulfenamide within the acidic canaliculi and adjacent to the target enzyme.

Omeprazole and lansoprazole are typically administered orally as delay-release capsules. The compounds are stable at a neutral pH, but are destroyed by gastric acid. Therefore, if the integrity of the gelatin-coated capsule is destroyed in any way and the patient swallows the enteric-coated grains, the neutral pH in the mouth and the esophagus will break down the microencapsulation, and the compounds will be degraded by the gastric acid in the stomach. The delay release capsules, when appropriately taken, release the omeprazole and lansoprazole after the granules leave the stomach.

Despite their good anti-secretory properties, proton pump inhibitors are not unanimously recognized as gastroprotective agents. In addition, there is a high relapse rate associated with treating gastrointestinal disorders with proton pump inhibitors as they do not eliminate *Helicobacter pylori* (*Campylobacter pylori*), the bacteria responsible for peptic ulcer disease, gastric lymphoma and adenocarcinoma.

A variety of adverse reactions have been ascribed to proton pump inhibitors, such as omeprazole and lansoprazole, reflecting, in part, the very large number of patients who have been treated with these drugs. The incidence of adverse reactions is low, and the adverse reactions are generally minor. Due to the profound reduction in gastric acidity, there tends to be an increased secretion of gastrin. Hence, patients who take therapeutic doses of omeprazole and lansoprazole have modest hypergastrinemia. Prolonged administration of high doses of the drugs can cause hyperplasia of oxyntic mucosal cells.

The most common side effects of proton pump inhibitors, such as omeprazole and lansoprazole, are nausea, diarrhea, abdominal colic, and central nervous system effects such as headaches and dizziness. Occasionally skin rashes and transient elevations of plasma activities of hepatic aminotransferase have been reported. The drugs can also result in bacterial overgrowth in the gastrointestinal tract and the development of nosocomial pneumonia.

There is a need in the art for proton pump inhibitors that have improved gastroprotective properties, decrease the recurrence of ulcers, facilitate ulcer healing and that can be used at low dosages. The invention is directed to these, as well as other, important ends.

SUMMARY OF THE INVENTION

The invention provides novel compounds that are proton pump inhibitors that are substituted with at least one nitrogen dioxide group ($NO_2$) (i.e., nitrosated), and pharmaceutically acceptable salts thereof. The proton pump inhibitors can be, for example, substituted benzimidazoles and substituted azabenzimidazoles, including, for example, omeprazole, pantoprazole, paniprazole, rabeprazole, leminoprazole, lansoprazole, timoprazole, tenatoprazole, disulprazole, esomeprazole, RO 18-5362 and IY 81149. The proton pump inhibitors can be nitrosated through one or more sites such as oxygen (hydroxyl condensation), sulfur (sulfhydryl condensation) and/or nitrogen. The invention also provides compositions comprising the novel compounds described herein in a pharmaceutically acceptable carrier.

The invention is also based on the discovery that administering at least one proton pump inhibitor that is substituted with at least one $NO_2$ group (i.e., nitrosated), and, optionally, at least one nitric oxide donor improves the properties of the proton pump inhibitor. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another embodiment of the invention provides compositions comprising at least one nitrosated proton pump inhibitor and at least one compound that donates, transfers or releases nitric oxide as a charged species, i.e., nitrosonium ($NO^+$) or nitroxyl ($NO^-$), or as the neutral species, nitric oxide (NO•), and/or stimulates endogenous production of nitric oxide or EDRF in vivo and/or is a substrate for nitric oxide synthase. The invention also provides for such compositions in a pharmaceutically acceptable carrier.

Yet another embodiment of the invention provides compositions comprising at least one proton pump inhibitor that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO^-$), or as the neutral species, nitric oxide (NO•), and/or is a substrate for nitric oxide synthase and/or at least therapeutic agent, including, but not limited to, nonsteroidal antiinflammatory compounds (NSAIDs), cyclooxygenase-2 (COX-2) inhibitors, antacids, bismuth-containing reagents, antibacterial compounds, $H_2$ receptor antagonists, *Helicobacter pylori* inhibitors, gastroprokinetic compounds, and mixtures of two or more thereof. The invention also provides for such compositions in a pharmaceutically acceptable carrier.

Yet another embodiment of the invention provides methods for treating gastrointestinal disorders, methods for improving the gastroprotective properties, anti-*Helicobacter* properties and antacid properties of proton pump inhibitors, methods for facilitating ulcer healing and methods for decreasing the rate of recurrence of ulcers in a patient in need thereof comprising administering to the patient a therapeutically effective amount of at least one proton pump inhibitor that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO^-$), or as the neutral species, nitric oxide (NO•), and/or stimulates endogenous production of nitric oxide or EDRF in vivo and/or is a substrate for nitric oxide synthase (i.e. NO donor). The methods can optionally further comprise the administration of at least one therapeutic agent, such as, for example, nonsteroidal antiinflammatory compounds (NSAID), selective COX-2 inhibitor, antacids, bismuth-containing reagents, antibacterial compounds, $H_2$ receptor antagonists, *Helicobacter pylori* inhibitors, gastroprokinetic compounds, and mixtures of two or more thereof. In this embodiment of the invention, the methods can involve administering the nitrosated proton pump inhibitors, administering the nitrosated proton pump inhibitors and NO donors, administering the nitrosated proton pump inhibitors and therapeutic agents, or administering the nitrosated proton pump inhibitors, NO donors, and therapeutic agents. The nitrosated proton pump inhibitors, nitric oxide donors, and/or therapeutic agents can be administered separately or as components of the same composition in one or more pharmaceutically acceptable carriers.

Yet another embodiment of the invention provides methods for decrease or reverse gastrointestinal toxicity resulting from the administration of nonsteroidal antiinflammatory compounds (NSAIDs) and/or selective COX-2 inhibitors, and methods for facilitating ulcer healing resulting from the administration of NSAIDs and/or selective COX-2 inhibitors, in a patient in need thereof comprising administering to the patient a therapeutically effective amount of at least one proton pump inhibitor that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO^-$), or as the neutral species, nitric oxide (NO•), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e. NO donor). The methods can optionally further comprise the administration of at least one therapeutic agent, such as, for example, nonsteroidal antiinflammatory compounds (NSAID), selective COX-2 inhibitors, antacids, bismuth-containing reagents, antibacterial compounds, $H_2$ antagonists, *Helicobacter pylori* inhibitors, gastroprokinetic compounds, and mixtures of two or more thereof. In this embodiment of the invention, the methods can involve administering the nitrosated proton pump inhibitors, administering the nitrosated proton pump inhibitors and NO donors, administering the nitrosated proton pump inhibitors and therapeutic agents, or administering the nitrosated proton pump inhibitors, NO donors, and therapeutic agents. The nitrosated proton pump inhibitors, nitric oxide donors, and/or therapeutic agents can be administered separately or as components of the same composition in one or more pharmaceutically acceptable carriers.

Yet another embodiment of the invention provides methods for treating bacterial infections and/or viral infections, in a patient in need thereof comprising administering to the patient a therapeutically effective amount of at least one proton pump inhibitor that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO^-$), or as the neutral species, nitric oxide (NO•), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e. NO donor). The methods can optionally further comprise the administration of at least one therapeutic agent, such as, for example, nonsteroidal antiinflammatory compounds (NSAID), selective COX-2 inhibitors, antacids, bismuth-containing reagents, antibacterial compounds, $H_2$ antagonists, *Helicobacter pylori* inhibitors, gastroprokinetic compounds, and mixtures of two or more thereof. In this embodiment of the invention, the methods can involve administering the nitrosated proton pump inhibitors, administering the nitrosated proton pump inhibitors and NO donors, administering the nitrosated proton pump inhibitors and therapeutic agents, or administering the nitrosated proton pump inhibitors, NO donors, and therapeutic agents. The nitrosated proton pump inhibitors, nitric oxide donors, and/or therapeutic agents can be administered separately or as components of the same composition in one or more pharmaceutically acceptable carriers.

In yet another embodiment the invention provides kits comprising at least one proton pump inhibitor that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO^-$), or as the neutral species, nitric oxide (NO•), and/or stimulates endogenous production of nitric oxide or EDRF in vivo and/or is a substrate for nitric oxide synthase. The kit can further comprise at least one therapeutic agent, such as, for example, nonsteroidal antiinflammatory compounds (NSAID), selective COX-2 inhibitors, antacids, bismuth-containing reagents, antibacterial compounds, H₂ antagonists, *Helicobacter pylori* inhibitors, gastroprokinetic compounds, and mixtures of two or more thereof. The nitrosated proton pump inhibitor, the nitric oxide donor and/or therapeutic agent, can be separate components in the kit or can be in the form of a composition in one or more pharmaceutically acceptable carriers.

These and other aspects of the invention are described in detail herein.

DETAILED DESCRIPTION OF THE INVENTION

As used throughout the disclosure, the following terms, unless otherwise indicated, shall be understood to have the following meanings.

"Gastrointestinal disorder" refers to any disease or disorder of the upper gastrointestinal tract of a patient including, for example, inflammatory bowel disease, Crohn's disease, gastritis, irritable bowel syndrome, constipation, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

"Upper gastrointestinal tract" refers to the esophagus, the stomach, the duodenum and the jejunum.

"Ulcers" refers to lesions of the upper gastrointestinal tract lining that are characterized by loss of tissue. Such ulcers include gastric ulcers, duodenal ulcers and gastritis.

"Viral infection" refers to both RNA and DNA viral infections. The RNA viral infections include, but are not limited to, orthomyxoviridae, paramyxoviridae, picornaviridae, rhabdoviridae, coronavaridae, togaviridae, bunyaviridae, arenaviridae and reteroviridae. The DNA viral infections include, but are not limited to, adenoviridae, proxviridae, papovaviridae, herpetoviridae and herpesviridae. The most preferable viral infections are those of the herpetoviridae family, such as, for example, herpes simplex viruses HSV-1 and HSV-2, cytomegalovirus (CMV), herpes varicella-zoster (VZV), Epstein-Barr (EBV), HHV6, HHV7, pseudorabies and rhinotracheitis, and the like.

"Proton pump inhibitor" refers to any compound that reversibly or irreversibly blocks gastric acid secretion by inhibiting the H⁺/K⁺-ATP ase enzyme system at the secretory surface of the gastric parietal cell.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Therapeutic agent" includes any therapeutic agent that can be used to treat or prevent the diseases described herein. "Therapeutic agents" include, for example, nonsteroidal antiinflammatory compounds (NSAID), selective COX-2 inhibitors, antacids, bismuth-containing reagents, antibacterial compounds, H₂ antagonists, *Helicobacter pylori* inhibitors gastroprokinetic compounds, and the like. Therapeutic agent includes the pro-drugs and pharmaceutical derivatives thereof including but not limited to the corresponding nitrosated and/or nitrosylated derivatives. Although nitric oxide donors have therapeutic activity, the term "therapeutic agent" does not include the nitric oxide donors described herein, since nitric oxide donors are separately defined.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 IC$_{50}$ of less than about 2 μM and a cyclooxygenase-1 IC$_{50}$ of greater than about 5 μM, in the human whole blood COX-2 assay (as described in Brideau et al., *Inflamm Res.*, 45: 68–74 (1996)) and also has a selectivity ratio of cyclooxygenase-2 inhibition over cyclooxygenase-1 inhibition of at least 10, and preferably of at least 40. In another embodiment, the compound has a cyclooxygenase-1 IC$_{50}$ of greater than about 1 μM, and preferably of greater than 20 μM. The compound can also inhibit the enzyme, lipoxygenase. Such selectivity may indicate an ability to reduce the incidence of common NSAID-induced side effects.

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide (NO⁺, NO⁻, NO•), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide (NO⁺, NO−, NO•), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$–$C_4$ hydrocarbon that can comprise one or two carbon-carbon double bonds.

"Substituted alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to —O⁻$R_{77}^+$ wherein $R_{77}$ is an organic or inorganic cation.

"Oxime" refers to =N—$OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to =N—$N(R_{81})(R'_{81})$ wherein $R'_{81}$ is independently selected from $R_{81}$, and $R_{81}$ is as defined herein.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, magnesium, calcium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino or arylalkylamino" refers to $R_{52}R_{55}N$—, wherein $R_{52}$ is an alkyl group, as defined herein, and $R_{55}$ is an aryl group, as defined herein.

"Alkylarylalkylamino" refers to $R_{52}R_{79}N$—, wherein $R_{52}$ is an alkyl group, as defined herein, and $R_{79}$ is an arylalkyl group, as defined herein.

"Alkylcycloalkylamino" refers to $R_{52}R_{80}N$—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2^-$.

"Sulfonic acid" refers to —S(O)$_2$OR$_{76}$, wherein R$_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —S(O)$_2$OR$_{58}$, wherein R$_{58}$ is an alkyl group, an aryl group, or an aryl heterocyclic ring, as defined herein.

"Sulfonamido" refers to —S(O)$_2$—N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to R$_{50}$S—, wherein R$_{50}$ is an alkyl group, as defined herein (preferably a lower alkyl group, as defined herein).

"Arylthio" refers to R$_{55}$S—, wherein R$_{55}$ is an aryl group, as defined herein.

"Arylalkylthio" refers to an aryl group, as defined herein, appended to an alkylthio group, as defined herein.

"Alkylsulfinyl" refers to R$_{50}$—S(O)—, wherein R$_{50}$ is an alkyl group, as defined herein.

"Alkylsulfonyl" refers to R$_{50}$—S(O)$_2$—, wherein R$_{50}$ is an alkyl group, as defined herein.

"Alkylsulfonyloxy" refers to R$_{50}$—S(O)$_2$—O—, wherein R$_{50}$ is an alkyl group, as defined herein.

"Arylsulfinyl" refers to R$_{55}$—S(O)—, wherein R$_{55}$ is an aryl group, as defined herein.

"Arylsulfonyl" refers to R$_{55}$—S(O)$_2$—, wherein R$_{55}$ is an aryl group, as defined herein.

"Arylsulfonyloxy" refers to R$_{55}$—S(O)$_2$—O—, wherein R$_{55}$ is an aryl group, as defined herein.

"Amidyl" refers to R$_{51}$C(O)N(R$_{57}$)— wherein R$_{51}$ and R$_{57}$ are each independently a hydrogen atom, an alkyl group, an aryl group or an arylheterocyclic ring, as defined herein.

"Ester" refers to R$_{51}$C(O)O— wherein R$_{51}$ is a hydrogen atom, an alkyl group, an aryl group or an arylheterocyclic ring, as defined herein.

"Carbamoyl" refers to —O—CO)N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ taken together are a heterocyclic ring, a cycloalkyl group or a bridged cycloalkyl group, as defined herein.

"Carboxyl" refers to —C(O)OR$_{76}$, wherein R$_{76}$ is a hydrogen, an organic cation or an inorganic cation, as defined herein.

"Carbonyl" refers to —C(O)—.

"Alkylcarbonyl" refers to R$_{52}$—C(O)—, wherein R$_{52}$ is an alkyl group, as defined herein.

"Arylcarbonyl" refers to R$_{55}$—C(O)—, wherein R$_{55}$ is an aryl group, as defined herein.

"Arylalkylcarbonyl" refers to R$_{55}$—R$_{52}$—C(O)—, wherein R$_{55}$ is an aryl group, as defined herein, and R$_{52}$ is an alkyl group, as defined herein.

"Alkylarylcarbonyl" refers to R$_{52}$—R$_{55}$—C(O)—, wherein R$_{55}$ is an aryl group, as defined herein, and R$_{52}$ is an alkyl group, as defined herein.

"Heterocyclicalkylcarbonyl" refer to R$_{78}$C(O)— wherein R$_{78}$ is a heterocyclicalkyl group, as defined herein.

"Carboxylic ester" refers to —C(O)OR$_{58}$, wherein R$_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{59}$)—C(O)N(R$_{51}$)(R$_{57}$) wherein R$_{51}$, R$_{57}$, and R$_{59}$ are each independently a hydrogen atom, an alkyl group, an aryl group or an arylheterocyclic ring, as defined herein, or R$_{51}$ and R$_{57}$ taken together are a heterocyclic ring, a cycloalkyl group or a bridged cycloalkyl group, as defined herein.

"Phosphoryl" refers to —P(R$_{70}$)(R$_{71}$)(R$_{72}$), wherein R$_{70}$ is a lone pair of electrons, thial or oxo, and R$_{71}$ and R$_{72}$ are each independently a covalent bond, a hydrogen, a lower alkyl, an alkoxy, an alkylamino, a hydroxy, an oxy or an aryl, as defined herein.

"Silyl" refers to —Si(R$_{73}$)(R$_{74}$)(R$_{75}$), wherein R$_{73}$, R$_{74}$ and R$_{75}$ are each independently a covalent bond, a lower alkyl, an alkoxy, an aryl or an arylalkoxy, as defined herein.

The compounds and compositions of the invention are novel and can be used to treat numerous gastrointestinal diseases and disorders. Such gastrointestinal disorders include, for example, inflammatory bowel disease, Crohn's disease, irritable bowel syndrome, ulcerative colitis, peptic ulcers, stress ulcers, bleeding peptic ulcers, duodenal ulcers, infectious enteritis, colitis, diverticulitis, gastric hyperacidity, gastric hyperacidity, dyspepsia, gastroparesis, Zollinger-Ellison syndrome, gastroesophageal reflux disease, *Helicobacter Pylori* associated disease, short-bowel (anastomosis) syndrome, hypersecretory states associated with systemic mastocytosis or basophilic leukemia and hyperhistaminemia that result, for example, from neurosurgery, head injury, severe body trauma or burns. The compounds and compositions of the invention can also be used as a pre-anesthetic medication in emergency operations to reduce the danger of aspiration of acidic gastric contents The proton pump inhibitors used in the compounds and compositions of the invention can be any of those known in the art, such as those exemplified herein.

Omeprazole, i.e., 5-methoxy-2((4-methoxy-3,5-dimethyl-2-pyridinyl)methyl)-sulfinyl)-1H-benzimidazole, (marketed under the trade name PRILOSEC® by Astra Merck, Wayne, Pa.) and lansoprazole, i.e., 2-(((3-methyl-4-(2,2,2-trifluoroethoxy)-2-pyridinyl)methyl)sulfinyl)-1H-benzimidazole (marketed under the trade name PREVACID® by TAP Pharmaceutical Inc., Deerfield, Ill.) are two of the most widely used compounds that inhibit gastric acid secretion. Other useful compounds include rabeprazole, i.e., 2-(((4-(3-methoxypropoxy)-3-methyl-2-pyridinyl)methyl)sulfinyl)-1H-benzimidazole (marketed under the trade name ACIPHEX® by Eisai, Inc.), pantoprazole, i.e., 5-(difluoromethoxy)-2-(((3,4-dimethoxy-2-pyridinyl)methyl)sulfinyl)-1H-benzimidazole, pariprazole, leminoprazole, timoprazole, tenatoprazole, disulprazole, esomeprazole (marketed under the trade name NEXIUM®), RO 18-5362, IY 81149. These compound do not exhibit anticholinergic or histamine $H_2$-receptor antagonist properties, but suppress gastric acid secretion by the specific inhibition of $(H^+, K^+)$-ATPase enzyme system at the secretory surface of the gastric parietal cell. As this enzyme system is regarded as the acid (proton) pump within the parietal cell, these substituted benzimidazoles have been characterized as gastric-acid-pump inhibitors as they block the final step of acid production. Although the proton pump inhibitor anti-secretory agents are effective in treating gastrointestinal disorders, they do not have any gastroprotective properties and, in addition, there is a high recurrence of ulcers associated with their use.

Another group of proton pump inhibitors are substituted quinolines, which include, for example, 3-butyl-4-(2-methylphenylamino)-8-(2-hydroxyethoxy)-quinoline.

Other proton pump inhibitors are disclosed in, for example, U.S. Pat. Nos. 4,045,564, 4,255,431, 4,634,710, 4,758,579, 4,806,549, 4,806,550, 4,818,760, 4,839,365, 4,845,118, 4,871,734, 4,873,337, 4,956,366, 4,981,861, 5,114,955, 5,149,702, 5,439,917, 5,554,631, 5,665,730, 5,677,302, 5,686,458, 5,703,097, 5,750,531, 5,990,311, 5,952,504 and 5,945,425 and in EP 0 005 129 A1, EP 0 033 094 B1, EP 0 045 200 A1, EP 0 221 041 A2, EP 0 234 485 A1, EP 0 246 774 A1, EP 0 254 588 A1, EP 0 259 174A1, EO 1 174,726A1, EP 1,166,287 A1, and in WO 89/08104, WO 92/12969, WO 94/27988, WO 95/01977, WO 95/27714, WO 97/32854, WO 98/18784, WO 98/43968, WO 98/54172, WO 01/85167; the disclosures of each of which are incorporated by reference herein in their entirety.

Several of the above contemplated proton pump inhibitors are described more fully in the literature, such as in Goodman and Gilman, The Pharmacological Basis of Therapeutics (9th Edition), McGraw-Hill, pages 901–915 (1996); Merck Index on CD-ROM, 13$^{th}$ Edition; STN Express, file phar and file registry, the disclosures of which are incorporated by reference herein in their entirety.

The proton pump inhibitors of invention are nitrosated through one or more sites such as oxygen (hydroxyl condensation), sulfur (sulfhydryl condensation), carbon and nitrogen. The proton pump inhibitor compounds that are nitrosated in accordance with the invention and/or are included in the compositions of the invention can be any of those known in the art, including those exemplified below.

In one embodiment, the invention describes nitrosated proton pump inhibitors of Formula (I) or a pharmaceutically acceptable salt thereof:

(I)

wherein
A is $S(O)_o$;
$W_1$ is $-C-NR_{87}R_{87}'$, $-CH$ or nitrogen;

$W_2$ is:

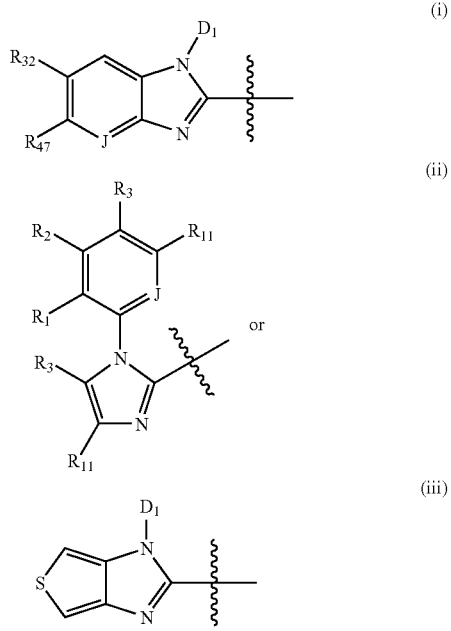

(i)

(ii)

or (iii)

J is CH or nitrogen;
o is an integer from 0 to 2;
$R_1$ is a hydrogen, an alkoxy group, a lower alkyl group, or an alkylthio group;
$R_2$ is a hydrogen, a halogen, an alkoxy group, a lower alkyl group, an alkylthio group, a haloalkoxy group, an alkoxyalkyl group, $-NR_{87}R_{87}'$, $-OX$, or $-SX$; or $R_2$ and $R_3$ taken together with the carbon atoms to which they are attached form a cycloalkyl ring, an aryl group or a heterocyclic ring; with the proviso that $R_2$ must be OX, or $-SX$ in $W_2$;
$R_3$ and $R_{11}$ are each independently a hydrogen, an alkoxy group, a lower alkyl group, or an alkylthio group; or $R_3$ and $R_{11}$ taken together with the carbon chain to which they are attached form a cycloalkyl ring, an aryl group or a heterocyclic ring;
$R_{32}$ and $R_{47}$ are each independently a hydrogen, an alkyl group, a halo group, an alkoxy group, a haloalkyl group, a haloalkoxy group, a cyano group, an aryl group, a heterocyclic ring, $-NR_{87}R_{87}'$, $-OX$, or $-CO_2R_{12}$; or $R_{32}$ and $R_{47}$ taken together are:

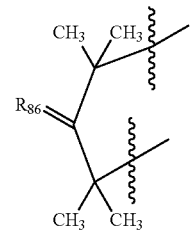

wherein
$R_{86}$ is oxygen or $N=O-R_{87}$;
$R_{87}$ and $R_{87}'$ are each independently hydrogen, a lower alkyl group, $D_1$ or X; or $R_{87}$ and $R_{87}'$ taken together with the nitrogen to which they are attached form a heterocyclic ring;

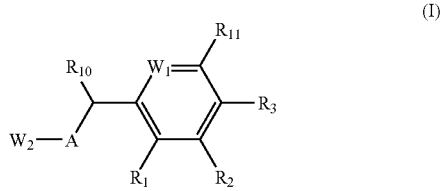

$R_{10}$ is a hydrogen; or $R_{10}$ and $R_1$ taken together with the carbon chain to which they are attached form a cycloalkyl ring;

$R_{12}$ is a lower alkyl group or X, with the proviso that Y in the definition of X must be oxygen or sulfur (—S—);

$D_1$ is:
(i) —C($R_6R_6'$)-T-C(O)—X;
(ii) —C(O)—X;
(iii) —S(O)$_2$—X;
(iv) —C($R_6R_6'$)-T-S(O)$_2$—X;
(v) —C($R_6R_6'$)—X; or
vi) an inorganic cation;

$R_6$ and $R_6'$ are each independently a hydrogen, a lower alkyl group, an aryl group;

X is:
(1) —Y—(CR$_4$R$_4'$)$_p$-T-(CR$_4$R$_4'$)$_p$—ONO$_2$;
(2) —Y—(CR$_4$R$_4'$)$_p$—ONO$_2$;

(3)
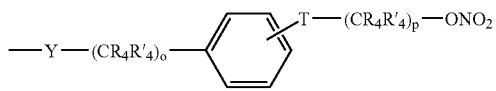

wherein T is ortho, meta or para;

(4)
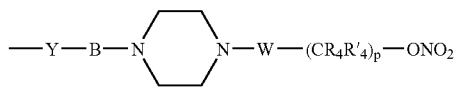

(5) —Y—(CR$_4$R$_4'$)$_p$—V—B-T-(CR$_4$R$_4'$)$_p$—ONO$_2$;
(6) —Y—(CR$_4$R$_4'$)$_p$-T-C(O)—(CR$_4$R$_4'$)$_o$—(CH$_2$)—ONO$_2$;
(7) —Y—(CR$_4$R$_4'$)$_p$—C(Z)-(CH$_2$)$_q$-T-(CR$_4$R$_4'$)$_q$—(CH$_2$)—ONO$_2$;
(8) —Y—(CR$_4$R$_4'$)$_p$-T-(CH$_2$)$_q$—V—(CR$_4$R$_4'$)$_q$—(CH$_2$)—ONO$_2$;
(9) —Y—(CR$_4$R$_4'$)$_p$—V—(CH$_2$)$_q$—V—(CR$_4$R$_4'$)$_q$—(CH$_2$)—ONO$_2$;
(10) —Y—(CR$_4$R$_4'$)$_o$—(W)$_q$—(CR$_4$R$_4'$)$_o$—(CH$_2$)—ONO$_2$;
(11) —NR$_j$—O—(CH$_2$)$_o$—V—(CR$_4$R$_4'$)$_q$—(CH$_2$)—ONO$_2$;
(12) —NR$_j$—O—(CH$_2$)$_o$—(W)$_q$—(CR$_4$R$_4'$)$_q$—(CH$_2$)—ONO$_2$;
(13) —O—NR$_j$—(CH$_2$)$_o$—(W)$_q$—(CR$_4$R$_4'$)$_q$—(CH$_2$)—ONO$_2$;
(14) —Y—(CH$_2$)$_o$—(W)$_q$—(CH$_2$)$_o$—V—(CR$_4$R$_4'$)$_o$-Q'-(CR$_4$R$_4'$)$_o$—(CH$_2$)—ONO$_2$;
(15) —Y—(CR$_4$R$_4'$)$_p$—V—(CH$_2$)$_o$—(W)$_q$—(CR$_4$R$_4'$)$_q$—CH$_2$)—ONO$_2$;
(16) —O—NR$_j$—(CH$_2$)$_o$—V—(CR$_4$R$_4'$)$_q$—(CH$_2$)—ONO$_2$;
(17) —Y—(CR$_4$R$_4'$)$_o$-Q'-(CR$_4$R$_4'$)$_o$—V—(CR$_4$R$_4'$)$_o$—(CH$_2$)—ONO$_2$;
(18) —Y—(CR$_4$R$_4'$)$_o$-Q'-(CR$_4$R$_4'$)$_o$—(W)$_q$—(CR$_4$R$_4'$)$_o$—(CH$_2$)—ONO$_2$;
(19) —Y—(CR$_4$R$_4'$)$_p$-T-(CR$_4$R$_4'$)$_p$-Q'-(CR$_4$R$_4'$)$_o$—(CH$_2$)—ONO$_2$;
(20) —Y—(CR$_4$R$_4'$)$_q$—C(Z)-(CR$_4$R$_4'$)$_o$—(CH$_2$)—ONO$_2$;
(21) —Y—(CR$_4$R$_4'$)$_p$-Q'-(CR$_4$R$_4'$)$_o$—(CH$_2$)—ONO$_2$;
(22) —Y—(CR$_4$R$_4'$)$_q$—P(O)MM';
(23) —Y—(CR$_4$R$_4'$)$_o$-Q'-(CR$_4$R$_4'$)$_o$—(CH$_2$)—ONO$_2$;
(24) —Y—(CR$_4$R$_4'$)$_o$-Q'-(CR$_4$R$_4'$)$_o$-T-(CR$_4$R$_4'$)$_o$—(CH$_2$)—ONO$_2$;
(25) —Y—(CR$_4$R$_4'$)$_q$—W)$_q$—(CR$_4$R$_4'$)$_o$-Q'-(CR$_4$R$_4'$)$_o$—(CH$_2$)—ONO$_2$;
(26) —Y—(CR$_4$R$_4'$)$_q$—V—(CR$_4$R$_4'$)$_o$-Q'-(CR$_4$R$_4'$)$_o$—(CH$_2$)—ONO$_2$;
(27) —Y—(CR$_4$R$_4'$)$_p$-(T)$_o$-(W)$_q$—(CR$_4$R$_4'$)$_o$—(CH$_2$)—ONO$_2$;
(28) —Y—(CR$_4$R$_4'$)$_p$—(W)$_q$-(T)$_o$-(CR$_4$R$_4'$)$_o$—(CH$_2$)—ONO$_2$;
(29) —Y—(CR$_4$R$_4'$)$_q$—C(Z)-V—(CR$_4$R$_4'$)$_q$—(CH$_2$)—ONO$_2$;
(30) —Y—(CR$_4$R$_4'$)$_o$—C(R$_4$)(ONO$_2$)—(CR$_4$R$_4'$)$_q$-(T)$_o$-(W)$_q$-(T)$_o$-(CR$_4$R$_4'$)$_o$—R$_5$;
(31) —Y—(CR$_4$R$_4'$)$_o$—V—(CR$_4$R$_4'$)$_o$-Q'-(CR$_4$R$_4'$)$_o$—(CH$_2$)—ONO$_2$;
(32) —Y—(CR$_4$R$_4'$)$_q$—C(Z)-Q'-(CR$_4$R$_4'$)$_o$—(CH$_2$)—ONO$_2$;
(33) —Y—(CR$_4$R$_4'$)$_p$—V—(CR$_4$R$_4'$)$_p$—(CH$_2$)—ONO$_2$;
(34) —Y—(CR$_4$R$_4'$)$_p$—V—(CH$_2$)$_q$-(T)$_o$-(CR$_4$R$_4'$)$_q$—CH$_2$)—ONO$_2$;
(35) —Y—(CR$_4$R$_4'$)$_p$-(T)$_o$-Q'-(T)$_o$-(CR$_4$R$_4'$)$_q$—(CH$_2$)—ONO$_2$;
(36) —Y—(CR$_4$R$_4'$)$_q$—C(Z)-(CR$_4$R$_4'$)$_q$—V—(CR$_4$R$_4'$)$_o$-Q'-(CR$_4$R$_4'$)$_o$—(CH$_2$)—ONO
(37) —Y—(CR$_4$R$_4'$)$_q$—C(Z)-(CR$_4$R$_4'$)$_q$—(W)$_q$—CR$_4$R$_4'$)$_o$-Q'-(CR$_4$R$_4'$)$_o$—(CH$_2$)—ONO$_2$;
(38) —NR$_j$—O—(CH$_2$)$_o$—V—(CR$_4$R$_4'$)$_o$-Q'-(CH$_2$)—ONO$_2$;
(39) —NR$_j$—O—(CH$_2$)$_o$—(W)$_q$—(CR$_4$R$_4'$)$_o$-Q'-(CH$_2$)—ONO$_2$;
(40) —O—NR$_j$—(CH$_2$)$_o$—(W)$_q$—(CR$_4$R$_4'$)$_o$-Q'-(CH$_2$)—ONO$_2$;
(41) —O—NR$_j$—(CH$_2$)$_o$—V—(CR$_4$R$_4'$)$_o$-Q'-(CH$_2$)—ONO$_2$;
(42) —NR$_j$—NR$_j$—(CR$_4$R$_4'$)$_p$—(W)$_q$-(T)$_o$-(CR$_4$R$_4'$)O—(CH$_2$)—ONO$_2$; or
(43) —Y—(CR$_4$R$_4'$)$_o$-Q'-(CR$_4$R$_4'$)$_o$—ONO$_2$; or
(44) —Y—(CR$_4$R$_4'$)$_o$—V—(CR$_4$R$_4'$)$_o$-Q-(CR$_4$R$_4'$)$_o$—ONO$_2$;

$R_4$ and $R_4'$ at each occurrence are independently a hydrogen, lower alkyl group, —OH, —CH$_2$OH, —ONO$_2$, —NO$_2$ or —CH$_2$ONO$_2$; or $R_4$ and $R_4'$ taken together with the carbon atom to which they are attached are a cycloalkyl group or a heterocyclic ring;

V is —C(O)-T-, -T-C(O)—, -T-C(O)-T or T-C(O)—CO)-T;

W is a covalent bond or a carbonyl group;

T at each occurrence is independently an oxygen, (S(O)$_o$)$_o$ or NR$_j$;

$R_j$ is a hydrogen, an alkyl group, an aryl group, a heterocyclic ring, an alkylcarbonyl group, an alkylaryl group, an alkylsulfinyl group, an alkylsulfonyl group, an arylsulfinyl group, an arylsulfonyl group, a sulfonamnido group, a N-alkylsulfonamido group, a N,N-diarylsulfonamido group, a N-arylsulfonamido group, a N-alkyl-N-arylsulfonamido group, a carboxamido group or a hydroxyl group;

p at each occurrence is independently an integer from 1 to 6;

q at each occurrence is independently an integer from 1 to 3;

Y is oxygen, sulfur (—S—), NR$_j$ or a covalent bond;

B is either phenyl or (CH$_2$)$_o$;

Q' is a cycloalkyl group, a heterocyclic ring or an aryl group;

Z is (=O), =N—OR$_5$), =N—NR$_5$R'$_5$) or (=CR$_5$R'$_5$);

M and M' are each independently —O$^-$H$_3$N$^+$—(CR$_4$R'$_4$)$_q$—CH$_2$ONO$_2$ or -T-(CR$_4$R'$_4$)$_o$—CH$_2$ONO$_2$;

R$_5$ and R$_5$' at each occurrence are independently a hydrogen, a hydroxyl group, an alkyl group, an aryl group, an alkylsulfonyl group, an arylsulfonyl group, a carboxylic ester, an alkylcarbonyl group, an arylcarbonyl group, a carboxamido group, an alkoxyalkyl group, an alkoxyaryl group, a cycloalkyl group or a heterocyclic ring;

o is as defined herein; and with the proviso that the compounds of Formula (I) must contain at least one nitrate group, and with the further proviso for compounds of Formula (I):

when D$_1$ is —C(R$_6$R$_6$')-T-C(O)—X, T is oxygen, R$_6$ and R$_6$' are each independently a hydrogen or a lower alkyl group, X is Formula 1, R$_4$ and R$_4$' are both hydrogen, Y cannot be oxygen, NR$_j$ or a covalent bond when T is oxygen;

when D$_1$ is —C(R$_6$R$_6$')—X, R$_6$ and R$_6$' are each independently a hydrogen or a lower alkyl group, X is Formula 2, R$_4$ and R$_4$' are both hydrogen, Y cannot be a covalent bond or oxygen; and with the proviso that the invention does not include the compounds of Formula (I), of ACS registry numbers 384339-54-2, 384339-53-1, 326850-42-4, 302543-91-5 and 301669-1. These compounds are disclosed in WO 02/00166, WO 01/12584, WO 00/61541, and WO 00/61537, the disclosures of each of which are incorporated by reference herein in their entirety.

In cases where multiple designations of variables which reside in sequence are chosen as a "covalent bond" or the integer chosen is 0, the intent is to denote a single covalent bond connecting one radical to another. For example, E$_0$ would denote a covalent bond, while E$_2$ denotes (E—E) and (C(R$_4$)(R$_4$))$_2$ denotes —C(R$_4$)(R$_4$)—C(R$_4$)(R$_4$)—.

Another embodiment of the invention describes nitrosated compounds of Formula (II) or pharmaceutically acceptable salts thereof:

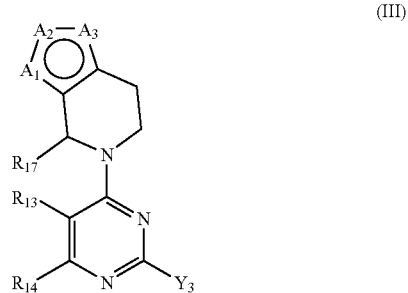

(II)

wherein

R$_x$ is hydrogen or

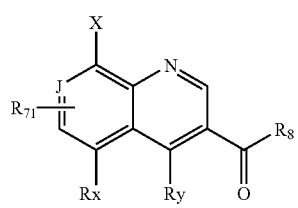

R$_y$ is hydrogen or

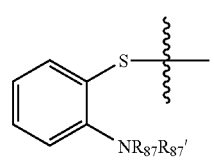

R$_8$ is a lower alkyl group, an alkoxyalkyl group, an alkylaryl group, a cycloalkyl group, a cycloalkylalkyl group, an aryl group, an alkylaryl group, or X;

R$_9$ at each occurrence is independently a hydrogen, a lower alkyl group, an akylthio group, a halogen, a cyano group an alkanoyl group, a haloalkyl group, a carbamoyl group, —NR$_{87}$X, —OX, or —CO$_2$R$_{12}$;

R$_{71}$ is a hydrogen, a lower alkyl group, an alkoxy group, or —OX;

d is an integer from 1 to 5; and wherein o, J, X, D$_1$, R$_{12}$, R$_{87}$, R$_{87}$' and o are as defined herein; and with the proviso that the compounds of Formula (II) must contain at least one nitrate group.

Another embodiment of the invention describes nitrosated compounds of Formula (III) or pharmaceutically acceptable salts thereof:

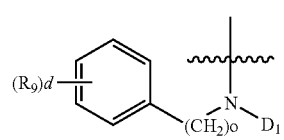

(III)

wherein

R$_{13}$ and R$_{14}$ are each independently a hydrogen a lower alkyl group, an alkoxyalkyl, or a lower alkyl-OX; or R$_{13}$ and R$_{14}$ taken together along with the carbon atoms to which they are attached form a cycloalkyl group or an aryl group;

R$_{17}$ is a hydrogen or a lower alkyl group;

Y$_3$ is:

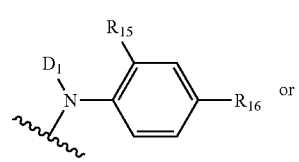

(a)

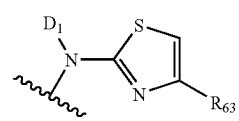

(b)

wherein

R$_{15}$ is a hydrogen or a lower alkyl group;

R$_{16}$ is a hydrogen, a halogen, or a lower alkyl group;

R$_{63}$ is a lower alkyl group or a phenyl group;

A$_1$, A$_2$ and A$_3$ comprise the other subunits of a 5- or 6-membered monocyclic aromatic ring and A$_1$, A$_2$ and A$_3$ are each independently:

(i) CR$_o$, wherein R$_o$ at each occurrence is hydrogen or —OX;

(ii) N—R$_p$, wherein R$_p$ at each occurrence is independently a covalent bond to an adjacent ring atom in order to render the ring aromatic, a hydrogen, or X;

(iii) a sulfur atom;

(iv) an oxygen atom; or
(v) $B_a=B_b$, wherein $B_a$ and $B_b$ are each independently a nitrogen atom or $CR_o$;
wherein $R_o$ at each occurrence is hydrogen or —OX;
$D_1$ and X are as defined herein, and
with the proviso that the compound of Formula (III) must contain at least one nitrate group.

Another embodiment of the invention describes nitrosated compounds of Formula (IV) or pharmaceutically acceptable salts thereof:

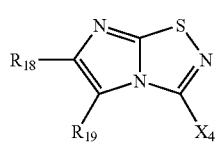

(IV)

wherein $R_{18}$ and $R_{19}$ at each occurrence are each independently a hydrogen, a lower alkyl group, a halogen, a nitro group, an alkoxy group, —OX, —NR$_{20}$R$_{21}$, —O(O)CR$_{20}$, —O(O)COR$_{20}$, —O(O)CNR$_{20}$R$_{21}$, —N(R$_{20}$)C(O)R$_{21}$, —N(R$_{20}$)C(O)NR$_{20}$R$_{21}$, or —N(R$_{20}$)C(O)OR$_{21}$; or $R_{18}$ and $R_{19}$ when taken together along with the carbons to which they are attached form a heterocyclic ring or a phenyl ring optionally substituted with up to four substituents selected from a hydrogen, a lower alkyl group, a halogen, a nitro group, an alkoxy group, —OD$_1$, —NR$_{20}$R$_{21}$, —O(O)CR$_{20}$, —O(O)COR$_{20}$, —O(O)CNR$_{20}$R$_{21}$, —N(R$_{20}$)C(O)R$_{21}$, —N(R$_{20}$)C(O)NR$_{20}$R$_{21}$ or —N(R$_{20}$)C(O)OR$_{21}$;

$R_{20}$ and $R_{21}$ at each occurrence are each independently a hydrogen, a lower alkyl group, an aryl group, a lower alkylaryl group, or X;

$X_4$ is —C(=R$_{86}$)R$_{22}$, a heterocyclic ring, —NR$_{20}$R$_{21}$, a halogen, an alkoxy group, an arylalkoxy group, a cycloalkoxy group, a heterocyclicalkoxy group, an alkylsulfonyl group, an alkylsulfinyl group, an arylsulfonyl group, an arylsulfinyl group an arylalkylsulfonyl group, an arylalkylsulfinyl group, a heterocyclicsulfonyl group, or a heterocyclicsulfinyl group;

$R_{22}$ is a hydrogen, an alkyl group, an alkoxy group, an aryl group, an alkylaryl group, a heterocyclic ring, an —O-heterocyclic ring, or an alkylheterocyclic ring;

$D_1$, $R_{86}$, and X are defined as herein, and with the proviso that the compound of Formula (IV) must contain at least one nitrate group.

Another embodiment of the invention describes nitrosated compounds of Formula (V) or pharmaceutically acceptable salt thereof:

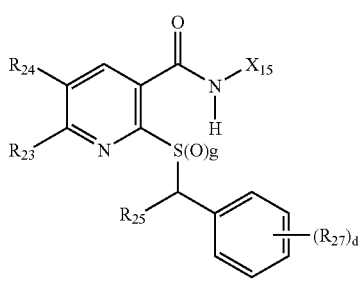

(V)

wherein
$X_{15}$ is:

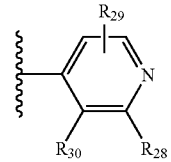

(a)

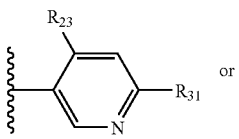

(b)

or

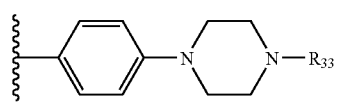

(c)

wherein
$R_{23}$ is a hydrogen, a dialkylamino group, —NR$_{87}$R$_{87}$', or a heterocyclic ring;
$R_{24}$ is a hydrogen or halogen;
$R_{25}$ is a hydrogen, —OX, or lower alkyl-OX;
$R_{27}$ at each occurrence is independently a hydrogen or an alkoxy group;
$R_{28}$, $R_{29}$, and $R_{30}$ are each independently a hydrogen, a lower alkyl group, a dialkylamino group, a heterocyclic ring, or a lower alkyl-OX;
$R_{31}$ is a hydrogen, a dialkylamino group, or an alkoxy group;
$R_{33}$ is a hydrogen or a lower alkyl group;
g is an integer from 0 to 1;
$R_{87}$, $R_{87}$', X and d are as defined herein, and
with the proviso that the compound of Formula (V) must contain at least one nitrate group.

Another embodiment of the invention describes nitrosated compounds of Formula (VI) or pharmaceutically acceptable salts thereof:

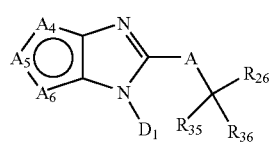

(VI)

wherein
$A_4$, $A_5$, and $A_6$ are each independently a sulfur or $CR_{34}$ with the proviso that at least one of $A_4$, $A_5$, or $A_6$ is a sulfur atom and the other two are $CR_{34}$;
$R_{34}$ at each occurrence is independently a hydrogen, a halogen, a cyano, a nitro, a trifluoromethyl, a lower alkyl group, a heterocyclic ring, a lower alkyl-OX, an alkoxy, a haloalkoxy, an alkylthio, an alkylsulfinyl, an alkylsulfonyl, an alkylcarbonyl, an alkoxycarbonyl, a carbamoyl, a N-alkylcarbamoyl, a N,N-di-alkylcarbamoyl, an ester, a cycloalkyl, an aryl, an alkylaryl, an aryloxy, an arylalkoxyoxy, an arylamino, a alkylarylamino, an arylthio, an arylsulfonyl, an arylsulfinyl, or a sulfonamido;

$R_{35}$ and $R_{36}$ are each independently a hydrogen or a lower alkyl group; or $R_{35}$ and $R_{36}$ taken together with the carbon chain to which they are attached form a cycloalkyl ring;

$R_{26}$ is:

(a)

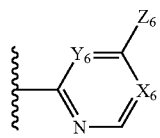

(b)

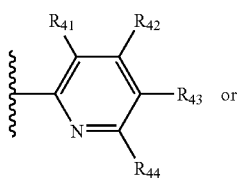 or (c)

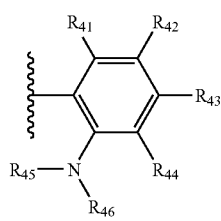

wherein $X_6$ is nitrogen, and $Y_6$ is $CR_{37}$; or $X_6$ is $CR_{37}$, and $Y_6$ is nitrogen;

$R_{37}$ is a hydrogen, a halogen, a lower alkyl group, a trifluoromethyl, an alkoxy group, a haloalkoxy group, an aryl group, an arylalkoxy group, a heterocyclic ring, or an aryloxy;

$Z_6$ is —$NR_{38}R_{39}$, $SR_{40}$, or an arylalkoxy group;

$R_{38}$ and $R_{39}$ are each independently a hydrogen, a lower alkyl group, an aryl group, an alkylaryl group, or a cycloalkyl group; or $R_{38}$ and $R_{39}$ taken together with the nitrogen to which they are attached form a heterocyclic ring;

$R_{40}$ is a hydrogen, a halogen, a lower alkyl group, an alkylaryl group, an alkenyl group, or a haloalkyl group;

$R_{41}$, $R_{42}$, $R_{43}$, and $R_{44}$ are each independently a hydrogen, a halogen, a lower alkyl group, an alkoxy group, a haloalkoxy group, an alkoxyaryl group, an alkylthio group, an alkysulfinyl group, an alkylsulfonyl group, a cyano group, $B_1$—OX, $B_1$—SX, —$B_1$—$NR_{20}R_{21}$, —$B_1$—O(O)$CR_{20}$, —$B_1$—O(O)$CNR_{20}R_{21}$, —$B_1$—N($R_{20}$)C(O)$R_{21}$, or —$B_1$—N($R_{20}$)S(O)$_2R_{21}$;

$R_{45}$ and $R_{46}$ are each independently a hydrogen, a lower alkyl group, a cycloalkyl group, an alkenyl group, or an alkynyl group;

$B_1$ is —C—$NR_{87}R_{87}'$ or nitrogen;

$D_1$, A, X, $R_{20}$, $R_{21}$, $R_{87}$ and $R_{87}'$ are as defined herein, and with the proviso that the compound of Formula (VI) must contain at least one nitrate group.

Another embodiment of the invention describes nitrosated compounds of Formula (VII) or pharmaceutically acceptable salts thereof:

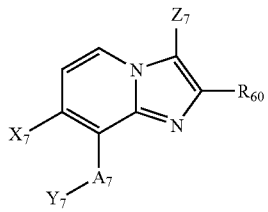

(VII)

wherein $R_{60}$ is a lower alkyl group, an aryl group, a haloalkyl group, a lower alkyl-OX, or heterocyclic ring;

$A_7$ is oxygen, —CH=CH— or —$ND_1$;

$X_7$ is a hydrogen or a halogen;

$Z_7$ is $CH_2OD$ or —$NDD_1$;

D is hydrogen, —$NO_2$ or $D_1$;

$Y_7$ is:

or $X_7$, $A_7$, and $Y_7$ taken together along with the carbon atoms to which they are attached is:

wherein $R_{61}$ is a hydrogen, a halogen, a lower alkyl group, —OX, or —NHC(O)O-lower alkyl;

$R_{62}$ is a hydrogen, a halogen, or a lower alkyl group; and wherein $D_1$ and X are as defined herein, and with the proviso that the compound of Formula (VII) must contain at least one nitrate group.

Another embodiment of the invention describes nitrosated compounds of Formula (VIII) or pharmaceutically acceptable salts thereof:

(VIII)

wherein $D_1$ and D are as defined herein, and with the proviso that the compound of Formula (VIII) must contain at least one nitrate group.

Another embodiment of the invention describes nitrosated compounds of Formula (IX) or pharmaceutically acceptable salts thereof:

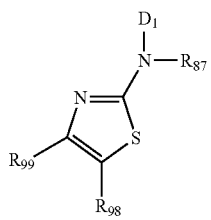
(IX)

wherein $R_{98}$ and $R_{99}$ taken together are:

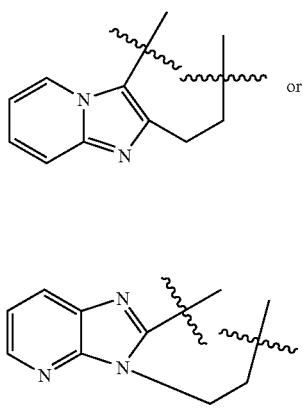

(i)

or (ii)

wherein $D_1$ and $R_{87}$ are as defined herein; and with the proviso that the compound of Formula (IX) must contain at least one nitrate group.

Another embodiment of the invention describes nitrosated compounds of Formula (X) or pharmaceutically acceptable salts thereof:

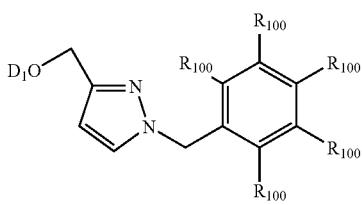
(X)

wherein $R_{100}$ at each occurrence is independently a hydrogen, a halogen, an alkoxy group or a haloalkoxy group;

wherein $D_1$ is as defined herein; and with the proviso that the compound of Formula (X) must contain at least one nitrate group.

Another embodiment of the invention describes nitrosated compounds of Formula (XI) or pharmaceutically acceptable salts thereof:

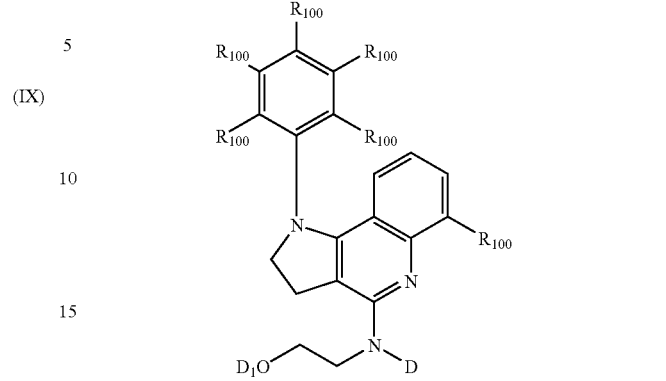
(XI)

wherein $R_{100}$, D and $D_1$ are as defined herein; and with the proviso that the compound of Formula (XI) must contain at least one nitrate group.

Another embodiment of the invention describes nitrosated compounds of Formula (XII) or pharmaceutically acceptable salts thereof:

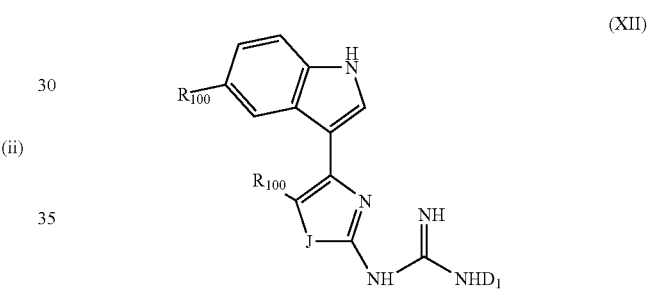
(XII)

wherein $R_{100}$, J and $D_1$ are as defined herein; and with the proviso that the compound of Formula (XII) must contain at least one nitrate group.

Another embodiment of the invention describes nitrosated compounds of Formula (XIII) or pharmaceutically acceptable salts thereof:

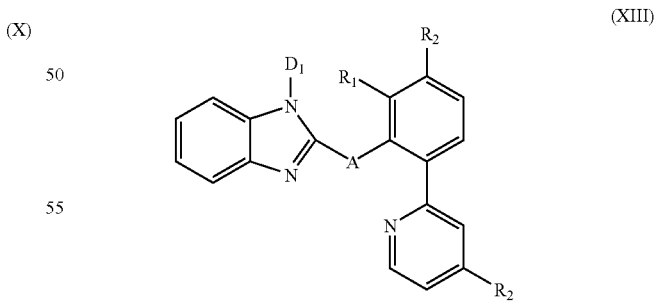
(XIII)

wherein $R_1$, $R_2$, A and $D_1$ are as defined herein; and with the proviso that the compound of Formula (XIII) must contain at least one nitrate group.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

It is also to be understood that the invention is intended to include within its scope compounds which may exist in more than one resonance form and the effects that the resonance form may have on the positions at $D_1$ or X substituents designated in the structures described herein.

In preferred embodiments for the compounds of Formulas (I), (II), (III), (IV), (V), (VI) (VII), (VIII), (IX), (X), (XI), (XII) and (XIII) and pharmaceutically acceptable salts thereof, X is:

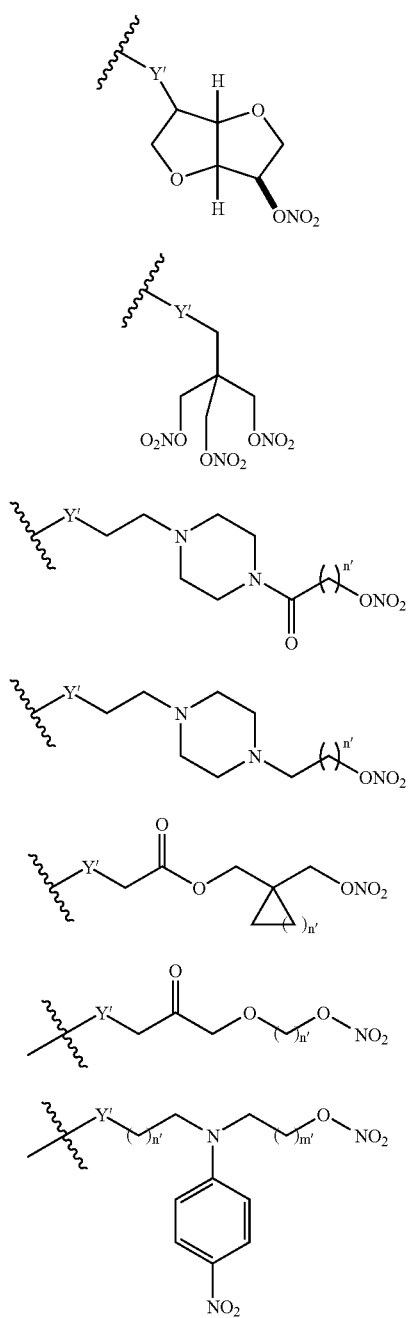

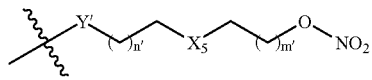

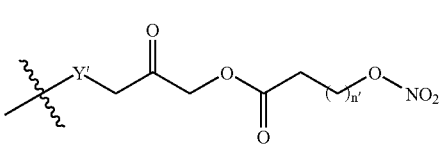

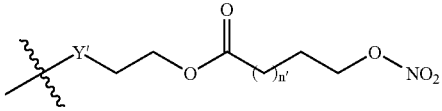

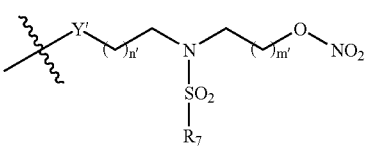

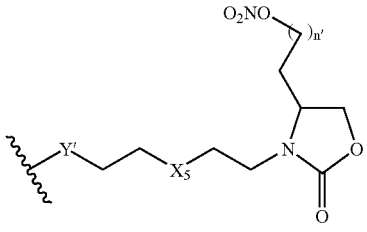

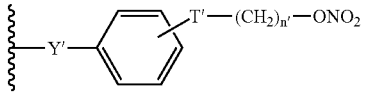

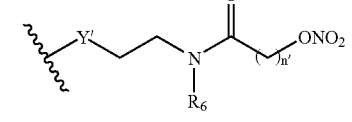

wherein T' maybe ortho, meta or para

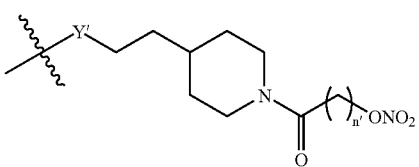

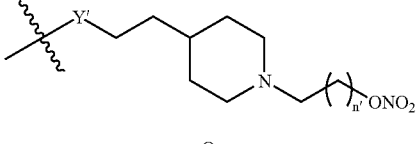

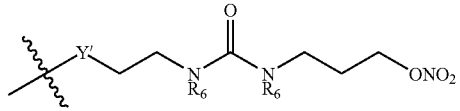

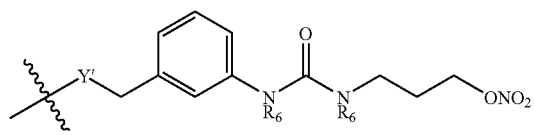
(18)
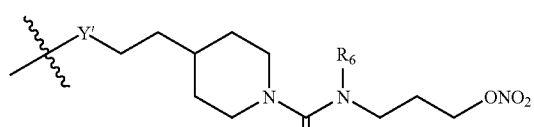
(19)
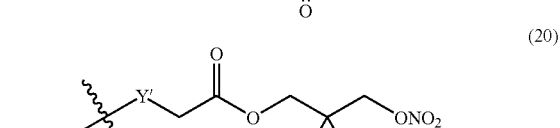
(20)
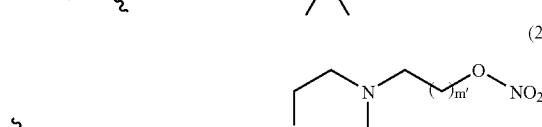
(21)
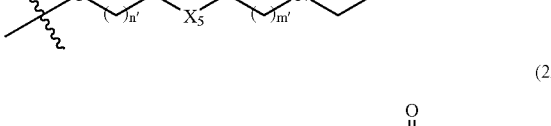
(22)
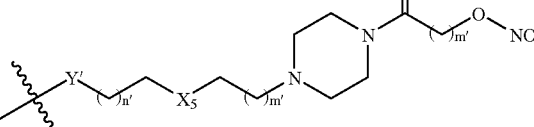
(23)
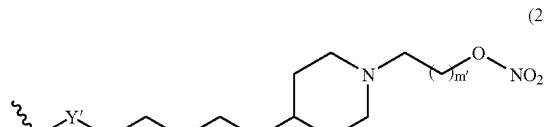
(24)
(25)
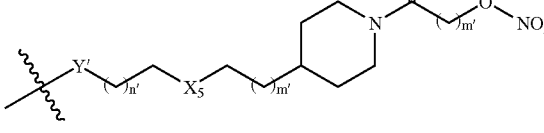
(26)
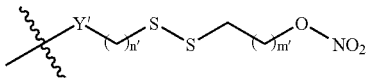
(27)
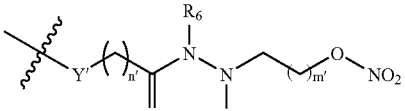
(28)
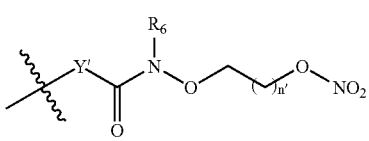
(29)
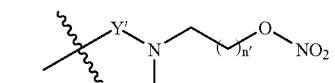
(30)
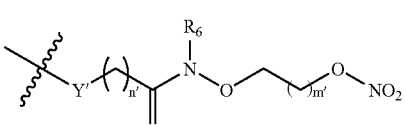
(31)
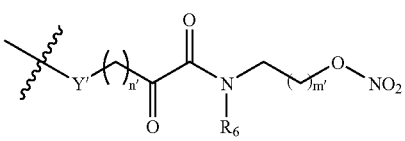
(32)
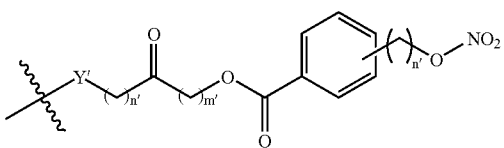
(33)
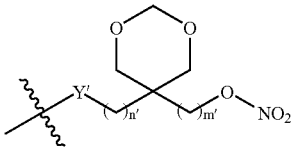
(34)
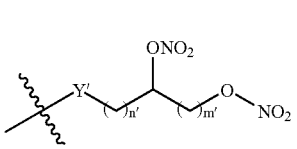
(35)
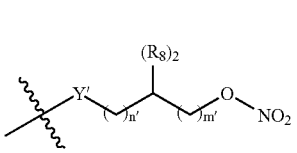
(36)
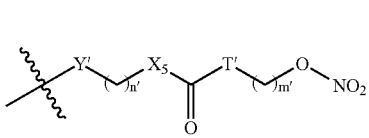
(37)

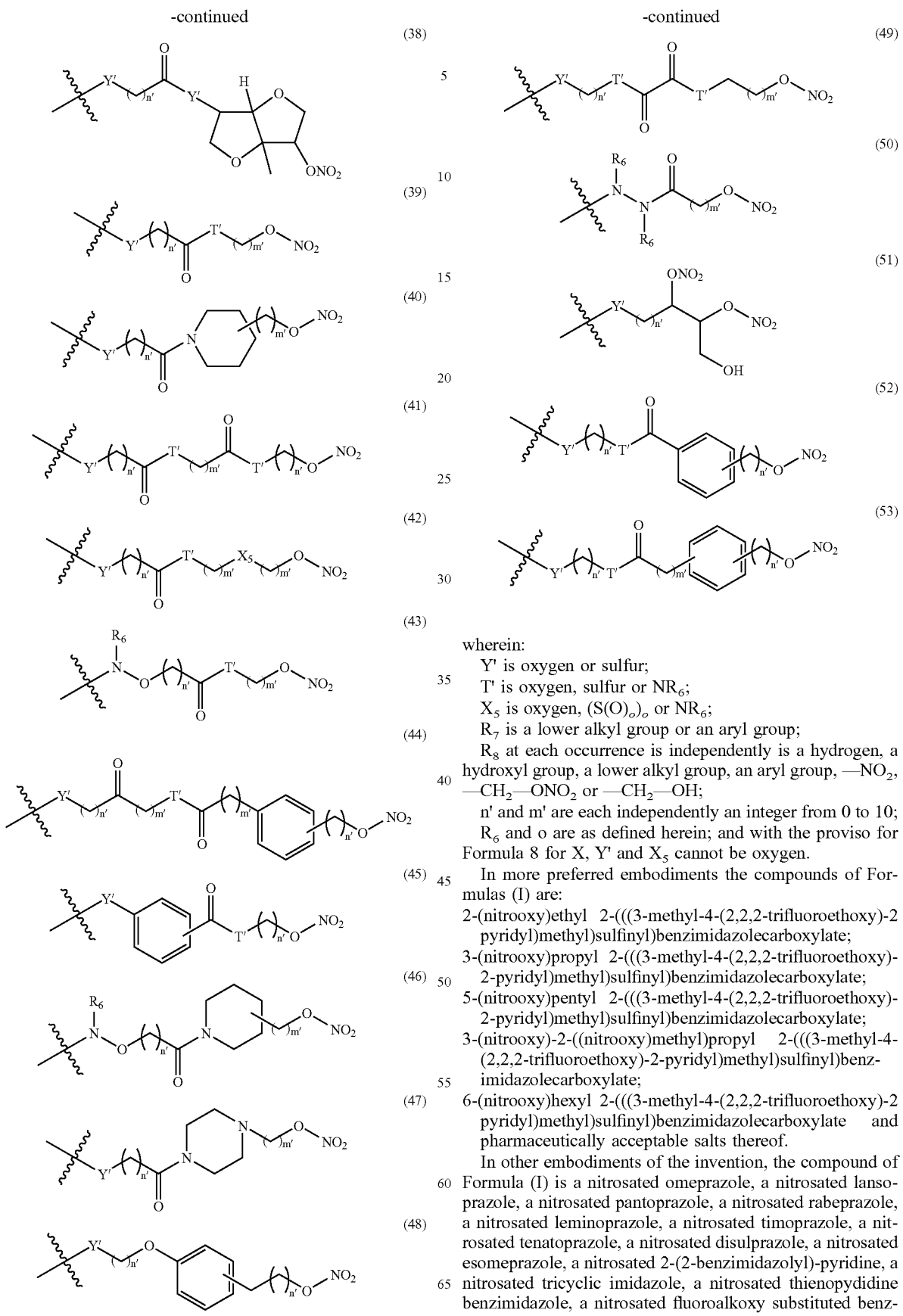

wherein:
Y' is oxygen or sulfur;
T' is oxygen, sulfur or NR₆;
X₅ is oxygen, (S(O)ₒ)ₒ or NR₆;
R₇ is a lower alkyl group or an aryl group;
R₈ at each occurrence is independently is a hydrogen, a hydroxyl group, a lower alkyl group, an aryl group, —NO₂, —CH₂—ONO₂ or —CH₂—OH;
n' and m' are each independently an integer from 0 to 10;
R₆ and o are as defined herein; and with the proviso for Formula 8 for X, Y' and X₅ cannot be oxygen.

In more preferred embodiments the compounds of Formulas (I) are:
2-(nitrooxy)ethyl 2-(((3-methyl-4-(2,2,2-trifluoroethoxy)-2 pyridyl)methyl)sulfinyl)benzimidazolecarboxylate;
3-(nitrooxy)propyl 2-(((3-methyl-4-(2,2,2-trifluoroethoxy)-2-pyridyl)methyl)sulfinyl)benzimidazolecarboxylate;
5-(nitrooxy)pentyl 2-(((3-methyl-4-(2,2,2-trifluoroethoxy)-2-pyridyl)methyl)sulfinyl)benzimidazolecarboxylate;
3-(nitrooxy)-2-((nitrooxy)methyl)propyl 2-(((3-methyl-4-(2,2,2-trifluoroethoxy)-2-pyridyl)methyl)sulfinyl)benzimidazolecarboxylate;
6-(nitrooxy)hexyl 2-(((3-methyl-4-(2,2,2-trifluoroethoxy)-2 pyridyl)methyl)sulfinyl)benzimidazolecarboxylate and pharmaceutically acceptable salts thereof.

In other embodiments of the invention, the compound of Formula (I) is a nitrosated omeprazole, a nitrosated lansoprazole, a nitrosated pantoprazole, a nitrosated rabeprazole, a nitrosated leminoprazole, a nitrosated timoprazole, a nitrosated tenatoprazole, a nitrosated disulprazole, a nitrosated esomeprazole, a nitrosated 2-(2-benzimidazolyl)-pyridine, a nitrosated tricyclic imidazole, a nitrosated thienopydidine benzimidazole, a nitrosated fluoroalkoxy substituted benzimidazole, a nitrosated dialkoxy benzimidazole, a nitrosated N-substituted 2-(pyridylalkenesulfinyl) benzimidazole, a nitrosated cycloheptenepyridine, a nitrosated 5-pyrrolyl-2-pyridylmethylsulfinyl benzimidazole, a nitrosated alkylsulfinyl benzimidazole, a nitrosated fluoro-pyridylmethylsulfinyl benzimidazole, a nitrosated imidazo(4,5-b) pydridine, a nitrosated RO 18-5362, a nitrosated Hoe-731, a nitrosated TY 11345, a nitrosated IY 81149 or a nitrosated NC-1300; the compound of Formula (II) is a nitrosated 4-amino-3-carbonyl quinoline, a nitrosated 4-amino-3-acyl-naphthyride, a nitrosated 4-aminoquinoline, a nitrosated 4-amino-3-acylquinoline, a nitrosated YJA-20379-8, a nitrosated YJA-20379-6 or a nitrosated 3-butyryl-4-(2-methylphenylamino)-8-(2-hydroxyethoxy)quinoline; the compound of Formula (III) is a nitrosated quinazoline, a nitrosated tetrahydroisoquinolin-2-yl pyrimidine or a nitrosated YH 1885; the compound of Formula (IV) is a nitrosated 3-substituted 1,2,4-thiadiazolo(4,5-a) benzimidazole or a nitrosated 3-substituted imidazo(1,2-d)-thiadiazole; the compound of Formula (V) is a nitrosated 2-sulfinylnicotinamide; the compound of Formula (VI) is a nitrosated pyridylsulfinylbenzimidazole, a nitrosated pyridylsulfinyl, a nitrosated thieno, a nitrosated imidazole, a nitrosated theinoimidazole-toluidine, a nitrosated 4,5-dihydrooxazole or a nitrosated thienoimidazole-toluidine; the compound of Formula (VII) is a nitrosated Sch 28080, a nitrosated imidazo (1,2-a)pyridine or a nitrosated pyrrolo(2,3-b)pyridine; the compound of Formula (VIII) is a nitrosated BE-18591, the compound of Formula (IX) is a nitrosated YJA-20379-5 or a nitrosated YJA-20379-2, the compound of Formula (X) is a nitrosated 1-((2-chlorophenyl)methyl)-1H-pyrazole-3-methanol, the compound of Formula (XI) is a nitrosated KR 60436 or a nitrosated DBM 819, the compound of Formula (XII) is a nitrosated (4-(1H-indol-3-yl)-5-methyl-2-thiazolyl-guanidine or a nitrosated (4-(5-(phenylmethoxy)-1H-indol-3-yl)-2-thiazolyl-guanidine, and pharmaceutically acceptable salts thereof.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

Another embodiment of the invention describes the metabolites of the compounds of Formulas (I), (II), (III), (IV), (V), (VI) (VII), (VIII), (IX), (X), (XI), (XII) and (XIII) and pharmaceutically acceptable salts thereof. These metabolites, include but are not limited to, the non-nitrosated derivatives, degradation products, hydrolysis products, and the like, of the compounds of Formulas (I), (II), (III), (IV), (V), (VI) (VII), (VIII), (IX), (X), (XI), (XII) and (XIII), and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I), (II), (III), (IV), (V), (VI) (VII), (VIII), (IX), (X), (XI), (XII) and (XIII)) can be synthesized by one skilled in the art following the methods and examples described herein. The synthesis of the non-nitrosated proton pump inhibitors are disclosed in, for example, U.S. Pat. Nos. 4,045,564, 4,255,431, 4,634,710, 4,758,579, 4,839,365, 4,873,337, 4,981,861, 5,149,702, 5,554,631, 5,703,097 and 5,945,425 and in EP 0 045 200 A1, EP 0 221 041 A2, EP 0 246 774 A1 and EP 0 254 588 A1 and in WO 98/54172 for the compounds of Formula (I); and in U.S. Pat. Nos. 4,806,549, 4,806,550 and 5,952,504 and in EP 0 259 174 A1 and in WO 89/08104 and WO 92/12969 for the compounds of Formula (II); and in U.S. Pat. Nos. 5,686,458, 5,750,531 and 5,990,311 and in WO 98/18784 and WO 98/43968 for the compounds of Formula (III); and in U.S. Pat. No. 5,677,302 for the compounds of Formula (IV); and in WO 97/32854 for the compounds of Formula (V); and in U.S. Pat. Nos. 4,818,760, 4,845,118, 4,871,734, 4,956,366 and 5,114,955 and in EP 0 234 485 A1 for the compounds of Formula (VI); and in U.S. Pat. Nos. 5,439, 917 and 5,665,730 and in EP 0 033 094 B1 and in WO 95/27714 for the compounds of Formula (VII); the disclosures of each of which are incorporated by reference herein in their entirety.

The nitrosated proton pump inhibitors of the invention can be synthesized as shown in reaction Schemes 1 through 7 presented herein. The proton pump inhibitor compounds can be nitrosated through one or more sites such as oxygen, sulfur, carbon and/or nitrogen using the methods described in the examples herein and using conventional methods known to one skilled in the art. For example, known methods for nitrosating compounds are described are described in U.S. Pat. Nos. 5,380,758, 5,859,053, 5,703,073 and 6,297,260; and in WO 94/03421, WO 94/04484, WO 94/12463, WO 95/09831, WO 95/30641, WO 97/27749, WO 98/19672, WO 01/00563, WO 00/51988, WO 00/72838, WO 01/04082, WO 01/10814, WO 01/45703, WO 02/11707, WO 02/30866 and Oae et al, *Org. Prep. Proc. Int.*, 15(3):165–198 (1983), the disclosures of each of which are incorporated by reference herein in their entirety. The methods of nitrosating the compounds described in the examples herein and in these references can be applied by one skilled in the art to produce any of the nitrosated proton pump inhibitors described herein.

Nitrate compounds of Formula (I), wherein $X_{16}$ is a —$ONO_2$ group and $R_1$, $R_2$, $R_3$, $R_{32}$, $R_{47}$, $R_{10}$, $R_{11}$, A, W, J, $R_e$, $R_f$, and p are as defined herein, and a nitrate containing carbamate is representative of the $D_1$ group, as defined herein, may be prepared as shown in Scheme 1. The substituted imidazole nitrogen group of Formula 1 is converted to the anion by treatment with one equivalent of a strong non-nucleophilic base, such as sodium hydride or potassium hydride, in an aprotic solvent, such as tetrahydrofuran (THF) or dimethylformamide (DMF). The carbamate of Formula IA wherein p, $R_e$ and $R_f$ are as defined herein, is prepared by reacting the imidazole anion with a suitably functionalized chloroformate in an inert solvent, such as TBF or DMF. Typically the coupling reaction is performed at a temperature ranging from −78° C. to room temperature. Preferred methods for the formation of chloroformates are reacting one equivalent of a $X_{16}$ functionalized alcohol with one equivalent of phosgene at a temperature ranging from −78° C. to 0° C. in an inert solvent, such as ether or THF and in the presence of an amine base, such as pyridine or triethylamine. Removal of the amine hydrochloride by filtration gives a solution of the desired chloroformate which may be used directly or concentrated and redissolved in the anhydrous solution of choice prior to the coupling reaction with the imidazole anion to give the carbamate of Formula IA.

On occasion it might be desirable to nitrosate the alcohol after coupling a chloroformate to the imidazole anion. The chloroformate would be prepared by reacting phosgene with an alcohol containing a protected alcohol moiety. Preferred protecting groups for an alcohol moiety are silyl ethers, such as trimethylsilyl ethers, tert-butyldimethylsilyl ethers, or tert-butyldiphenylsilyl ethers. After formation of the carbamate, deprotection of the hydroxyl moiety (fluoride ion is the preferred method for removing silyl ether protecting groups) followed by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula IA. Alternately, nitrosation of the carbamate product may be accomplished by first converting the deprotected alcohol to a leaving group such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccimide, in an inert solvent, such as THF. Treatment of the bromide or iodide with silver nitrate in an inert solvent, such as acetonitrile, gives the compound of Formula IA. Alternatively, the halide containing carbamate may be formed directly by preparing a halide containing chloroformate from a halide containing alcohol. Preferred halides are bromide and iodide. Coupling of the imidazole anion with the halide containing chloroformate followed by reaction of the carbamate product with silver nitrate in an inert solvent, such as acetonitrile, gives the compound of Formula IA.

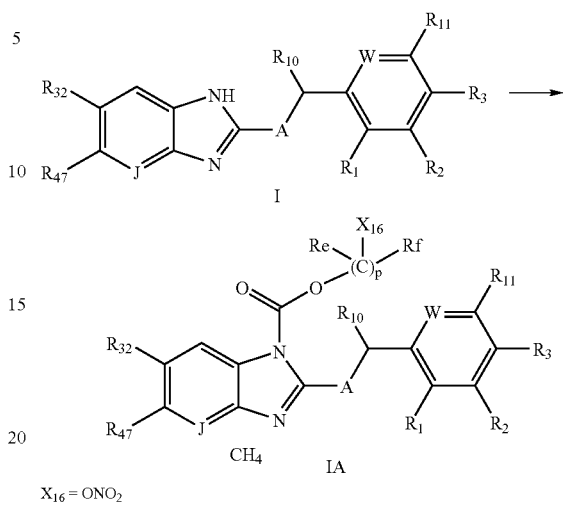

Scheme 1

Nitrate compounds of Formula (II), where $X_{16}$ is a —$ONO_2$ group and $R_8$, $R_9$, $R_{71}$, $D_1$, J, $R_e$, $R_f$ o, and d are as defined herein and p is an integer from 0 to 10, and a nitrate containing alkoxyethyl ester is representative of the X group, as defined herein, may be prepared as shown in Schemes 2 and 2A. The hydroxyl group of Formula 2 is converted to the ester of Formula IIA, where p, $R_e$, $R_f$ and $X_{16}$ are as defined herein, by reaction with an appropriate nitrate containing activated acylating agent. Preferred methods for the formation of esters are reacting the alcohol with the preformed acid chloride or anhydride of the nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate such as isobutylchloroformate in the presence of an amine base, such as triethylamine in an inert solvent, such as ether, THF, dichloromethane, or toluene. Alternatively, the alcohol and nitrate containing acid may be condensed in the presence of a dehydrating agent, such as dicyclohexylcarbodiimide (DCC) or 1-ethyl-3 (3-dimethylaminopropyl) carbodiimide hydrochloride (EDAC.HCl) with or without a catalyst, such as 4-dimethylaminopyridine (DMAP) or 1-hydroxybenzotriazole (HOBt).

On occasion it might be desirable to nitrosate the alcohol after coupling the activated acylating agent to the alcohol. The activated acylating agent would be from an acid containing a protected alcohol moiety. Preferred protecting groups for an alcohol moiety are silyl ethers, such as trimethylsilyl ethers, tert-butyldimethylsilyl ethers, or tert-butyldiphenylsilyl ethers. After. formation of the ester, deprotection of the hydroxyl moiety (fluoride ion is the preferred method for removing silyl ether protecting groups) followed by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula IIA. Alternately, nitrosation of the ester product may be accomplished by first converting the deprotected alcohol to a leaving group such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccimide, in an inert solvent, such as THF. Treatment of the bromide or iodide with silver nitrate in an inert solvent, such as acetonitrile, gives the compound of Formula IIA. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile gives the compound of Formula IIA. Preferred coupling methods for the formation of esters from alcohols are those methods described herein (e.g. with the preformed acid chloride or anhydride or with the carboxylic acid and a dehydration agent, such as DCC or EDAC.HCl).

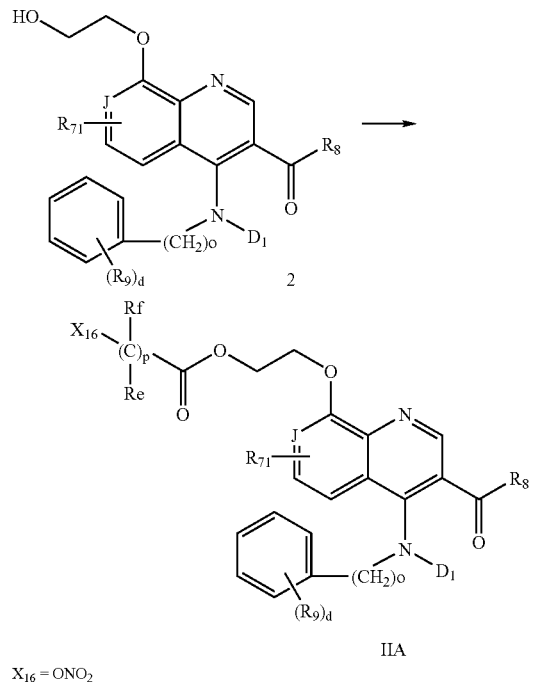

Scheme 2

$X_{16} = ONO_2$

Alternately, nitrosation of the alcohol in Formula 2 by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula IIB as shown in Scheme 2A.

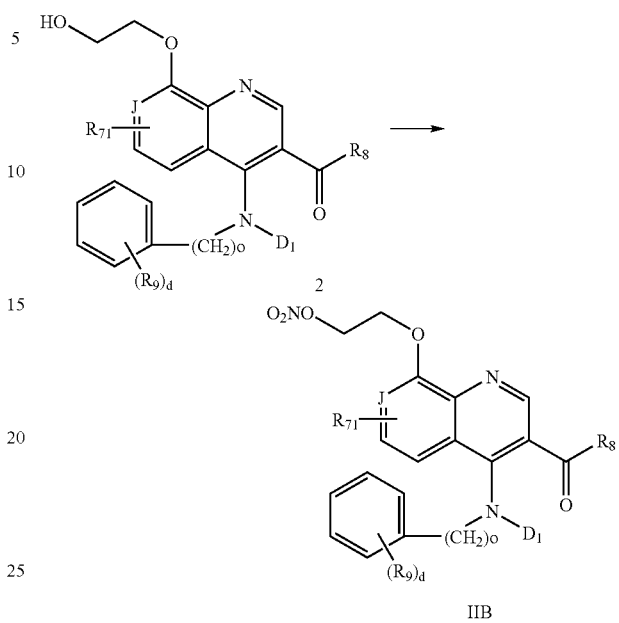

Scheme 2A

Nitrate compounds of Formula (III), wherein $X_{16}$ is a —$ONO_2$ group and $R_{14}$, $R_{17}$, $A_1$, $A_2$, $A_3$, $R_e$, $R_f$, $Y_3$, and p, are as defined herein, and a nitrate containing acyloxymethyl ester is representative of the $R_{13}$ group may be prepared as shown in Schemes 3 and 3A. The hydroxyl group of Formula 3 is converted to the ester of Formula IIIA, where p, $R_e$, $R_f$ and $X_{16}$ are as defined herein, by reaction with an appropriate nitrate containing activated acylating agent. Preferred methods for the formation of esters are reacting the alcohol with the preformed acid chloride or symmetrical anhydride of the nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate, such as isubutylchloroformate, in the presence of an amine base, such as triethylamine in an inert solvent solvent, such as ether, THF, dichloromethane, or toluene. Alternatively, the alcohol and nitrate containing acid may be condensed in the presence of a dehydrating agent, such as DCC or EDAC.HCl with or without a catalyst, such as DMAP or HOBt.

On occasion it might be desirable to nitrosate the alcohol after coupling the activated acylating agent to the alcohol. The activated acylating agent would be from an acid containing a protected alcohol moiety. Preferred protecting groups for an alcohol moiety are silyl ethers, such as trimethylsilyl ethers, tert-butyldimethylsilyl ethers, or tert-butyldiphenylsilyl ethers. After formation of the ester, deprotection of the hydroxyl moiety (fluoride ion is the preferred method for removing silyl ether protecting groups) followed by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula IIIA. Alternately, nitrosation of the ester product may be accomplished by first converting the deprotected alcohol to a leaving group such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccimide, in an inert solvent, such as THF. Treatment of the bromide or iodide with silver nitrate in an inert solvent, such as acetonitrile, gives the compound of Formula IIIA. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile gives the compound of Formula IIIA. Preferred coupling methods for the formation of esters from alcohols are those methods described herein (e.g. with the preformed acid chloride or anhydride or with the carboxylic acid and a dehydration agent, such as DCC or EDAC.HCl).

Scheme 3

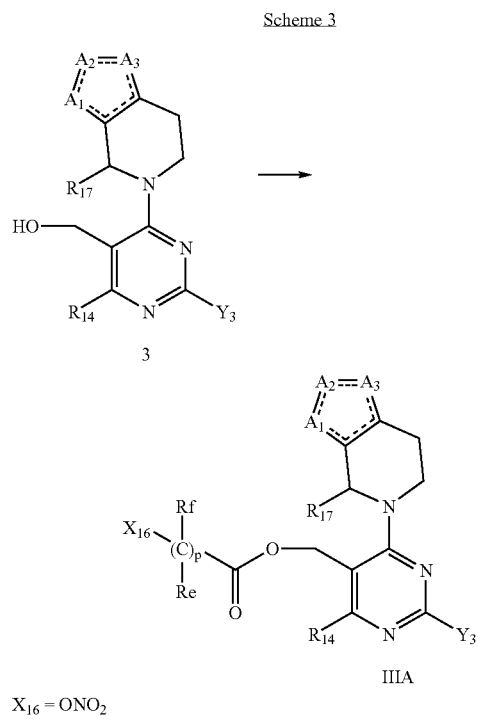

$X_{16} = ONO_2$

Alternately, nitrosation of the alcohol product in Formula 3 by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula IIIB as shown in Scheme 3A.

Scheme 3A

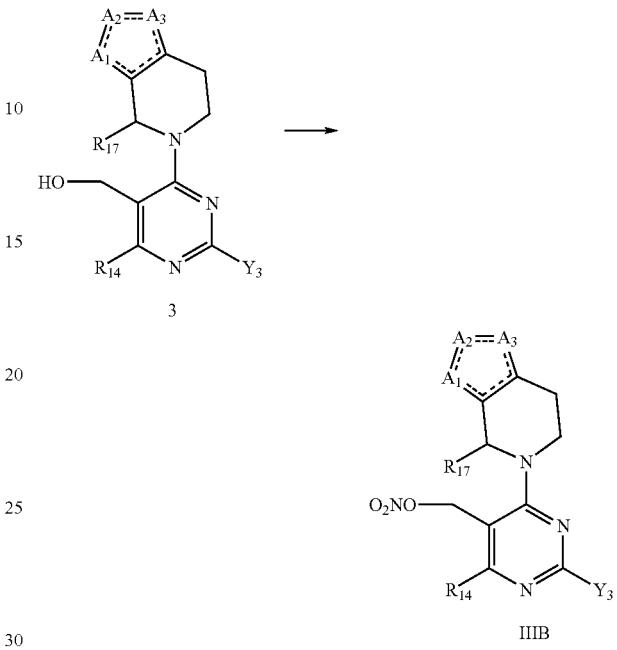

Nitrate compounds of Formula (IV), wherein $X_{16}$ is a —$ONO_2$ group and $R_{18}$, $R_{19}$, $R_e$, $R_f$ and p, are as defined herein, and a nitrate containing carboxylic acid ester is representative of the $X_4$ group may be prepared as shown in Scheme 4. The acid of the Formula 4 is converted to the ester of Formula IVA, where p, $R_e$, $R_f$ and $X_{16}$ are as defined herein, by reaction with an appropriate nitrate containing alcohol. Preferred methods for the preparation of esters are initially forming the mixed anhydride via reaction of 4 with a chloroformate, such as isobutylchloroformate, in the presence of a non nucleophilic base, such as triethylamine, in an anhydrous inert solvent, such as dichloromethane, diethylether or THF. The mixed anhydride is then reacted with the nitrate containing alcohol preferably in the presence of a condensation catalyst, such as DMAP. Alternatively, the acid 4 may be first converted to the acid chloride by treatment with oxalyl chloride in the presence of a catalytic amount of DMF. The acid chloride is then reacted with the nitrate containing alcohol preferably in the presence of a condensation catalyst, such as DMAP, and a tertiary amine base, such as triethylamine, to give the ester of Formula IVA. Alternatively, the acid 4 and nitrate containing alcohol may be coupled to give the ester of Formula IVA, by treatment with a dehydration agent, such as DCC or EDAC.HCl, with or without a catalyst, such as DMAP or HOBt.

On occasion it might be desirable to nitrosate the alcohol after coupling the acid to the alcohol. The ester would be prepared by reacting the carboxylic acid with an alcohol containing a protected alcohol moiety. Preferred protecting groups for an alcohol moiety are silyl ethers, such as a trimethylsilyl ether, a tert-butyldimethylsilyl ether, or a tert-butyldiphenylsilyl ether. After coupling the acid and alcohol moieties, deprotection of the hydroxyl moiety (fluoride ion is the preferred method for removing silyl ether protecting groups) followed by reaction with a suitable nitrosating agent, with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula IVA. Alternately, nitrosation of the ester product containing a deprotected alcohol moiety may be accomplished by first converting the alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccimide, in an inert solvent, such as THF. Treatment of the bromide or iodide with silver nitrate in an inert solvent, such as acetonitrile, gives the compound of Formula IVA. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate gives the compound of Formula IVA. Preferred coupling methods for the formation of esters from alcohols are those methods described herein (e.g. with the preformed acid chloride or anhydride or with the carboxylic acid and a dehydration agent, such as DCC or EDAC.HCl).

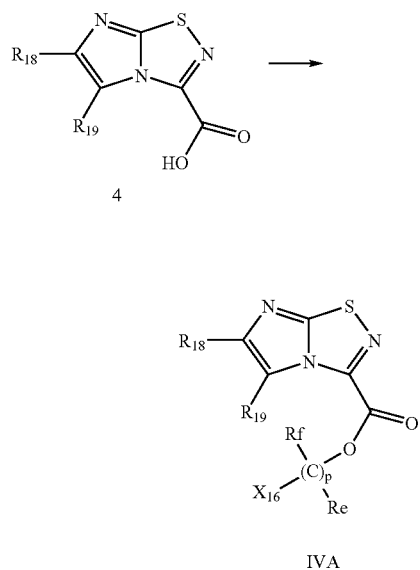

Scheme 4

4

IVA $X_{16} = ONO_2$

Nitrate compounds of Formula (V), wherein $X_{16}$ is a —$ONO_2$ group and $R_{23}$, $R_{24}$, $R_{25}$, $R_{27}$, $R_{29}$, $R_{30}$, $R_e$, $R_f$, g, dand p, are as defined herein, and a nitrate containing ester of a substituted pyridine is representative of the $X_{15}$ group may be prepared as shown in Schemes 5 and 5A. The hydroxyl group of Formula 5 is converted to the ester of Formula VA, where p, $R_e$, $R_f$ and $X_{16}$ are as defined herein, by reaction with an appropriate nitrate containing activated acylating agent. Preferred methods for the formation of esters are reacting the alcohol with the preformed acid chloride or symmetrical anhydride of the nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate, such as isubutylchloroformate, in the presence of an amine base, such as triethylamine, in an inert solvent solvent, such as ether, THF, dichloromethane, or toluene. Alternatively, the alcohol and nitrate containing acid may be condensed in the presence of a dehydrating agent, such as DCC or EDAC.HCl, with or without a catalyst, such as DMAP or HOBt.

On occasion it might be desirable to nitrosate the alcohol after coupling the activated acylating agent to the alcohol. The activated acylating agent would be prepared from an acid containing a protected alcohol moiety. Preferred protecting groups for an alcohol moiety are silyl ethers, such as a trimethylsilyl ether, a tert-butyldimethylsilyl ether, or a tert-butyldiphenylsilyl ether. After formation of the ester, deprotection of the hydroxyl moiety (fluoride ion is the preferred method for removing silyl ether protecting groups) followed by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula VA. Alternately, nitrosation of the ester product may be accomplished by first converting the deprotected alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine in the presence of a halide source, such as carbon tetrabromide or N-iodosuccimide in an inert solvent, such as THF. Treatment of the bromide or iodide with silver nitrate in an inert solvent, such as acetonitrile, gives the compound of Formula VA. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile, gives the compound of Formula VA. Preferred coupling methods for the formation of esters from alcohols are those methods described herein (e.g. with the preformed acid chloride or anhydride or with the carboxylic acid and a dehydration agent, such as DCC or EDAC.HCl).

Scheme 5

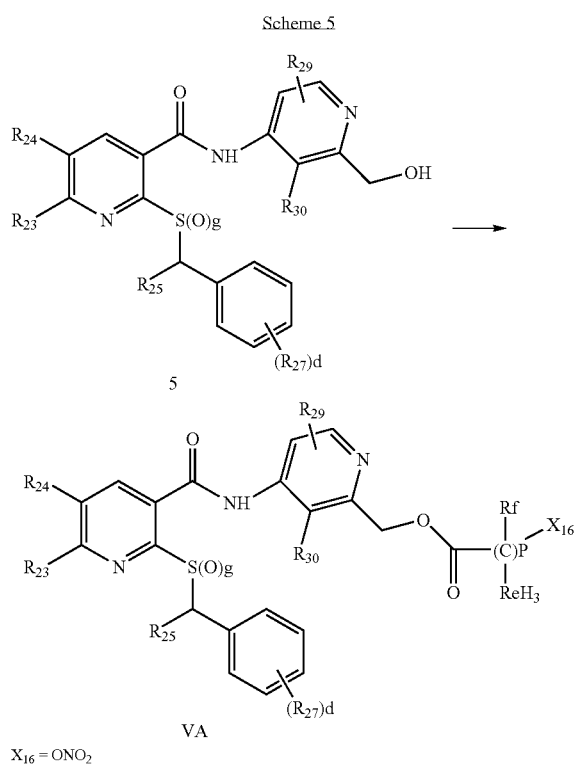

$X_{16}$ = ONO$_2$

Alternately, nitrosation of the alcohol product in Formula 5 by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula VB as shown in Scheme 5A.

Scheme 5A

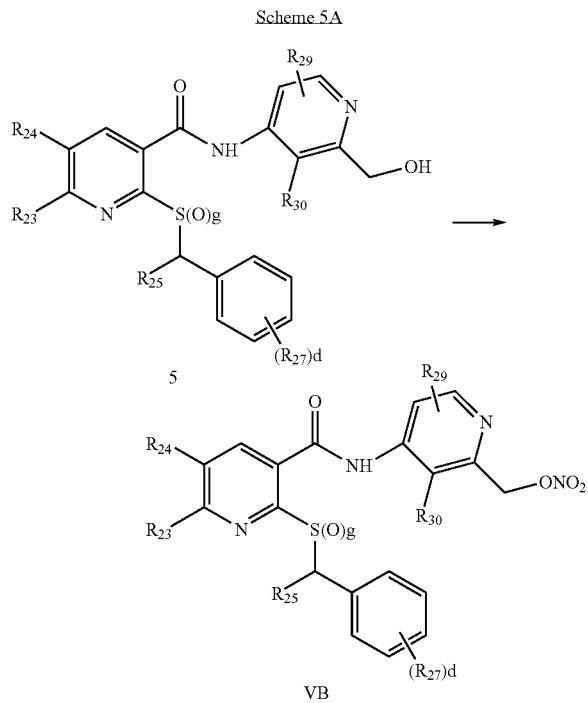

Nitrate compounds of Formula (VI), wherein $X_{16}$ is a —ONO$_2$ group and $R_{26}$, $R_{35}$, $R_{36}$, A, $A_4$, $A_5$, $A_6$, $R_e$, $R_f$, and p are as defined herein, and a nitrate containing carbamate is representative of the $D_1$ group, as defined herein, may be prepared as shown in Scheme 6. The substituted imidazole nitrogen group of Formula 6 is converted to the anion by treatment with one equivalent of a strong non-nucleophilic base, such as sodium hydride or potassium hydride in an aprotic solvent, such as THF or DMF. The carbamate of Formula VIA wherein p, $X_{16}$, $R_e$ and $R_f$ The carbamate of Formula VIA wherein p, $R_e$ and $R_f$ are as defined herein, is prepared by reacting the imidazole anion with a suitably functionalized chloroformate in an inert solvent, such as THF or DMF. Typically the coupling reaction is performed at a temperature ranging from −78° C. to room temperature. Preferred methods for the formation of chloroformates are reacting one equivalent of a $X_{16}$ functionalized alcohol with one equivalent of phosgene at a temperature ranging from −78° C. to 0° C. in an inert solvent, such as ether or THF and in the presence of an amine base, such as pyridine or triethylamine. Removal of the amine hydrochloride by filtration gives a solution of the desired chloroformate which may be used directly or concentrated and redissolved in the anhydrous solution of choice prior to the coupling reaction with the imidazole anion to give the carbamate of Formula VIA.

On occasion it might be desirable to nitrosate the alcohol after coupling a chloroformate to the imidazole anion. The chloroformate would be prepared by reacting phosgene with an alcohol containing a protected alcohol moiety. Preferred protecting groups for an alcohol moiety are silyl ethers, such as trimethylsilyl ethers, tert-butyldimethylsilyl ethers, or tert-butyldiphenylsilyl ethers. After formation of the carbamate, deprotection of the hydroxyl moiety (fluoride ion is the preferred method for removing silyl ether protecting groups) followed by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from −20° C. to room temperature, gives the compound of Formula VIA. Alternately, nitrosation of the carbamate product may be accomplished by first converting the deprotected alcohol to a leaving group such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccinimide, in an inert solvent, such as THF. Treatment of the bromide or iodide with silver nitrate in an inert solvent, such as acetonitrile, gives the compound of Formula VIA. Alternatively, the halide containing carbamate may be formed directly by preparing a halide containing chloroformate from a halide containing alcohol. Preferred halides are bromide and iodide. Coupling of the imidazole anion with the halide containing chloroformate followed by reaction of the carbamate product with silver nitrate in an inert solvent, such as acetonitrile, gives the compound of Formula VIA.

Scheme 6

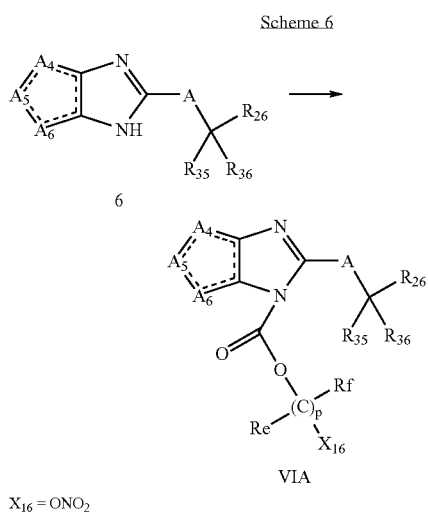

$X_{16} = ONO_2$

Nitrate compounds of Formula (VII), wherein $X_{16}$ is a —$ONO_2$ group and $R_{60}$, $A_7$, $X_7$, $Y_7$, $R_e$, $R_f$ and p, are as defined herein, and a nitrate containing acyl group is representative of the D group may be prepared as shown in Schemes 7 and 7A. The hydroxyl group of Formula 7 is converted to the ester of Formula VIIA, wherein p, $R_e$ $R_f$ and $X_{16}$ are as defined herein, by reaction with an appropriate nitrate containing activated acylating agent. Preferred methods for the formation of esters are reacting the alcohol with the preformed acid chloride or symmetrical anhydride of the nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate, such as isubutylchloroformate, in the presence of an amine base, such as triethylamine, in an inert solvent solvent, such as ether, THF, dichloromethane, or toluene. Alternatively, the alcohol and nitrate containing acid may be condensed in the presence of a dehydrating agent, such as DCC or EDAC.HCl with or without a catalyst, such as DMAP or HOBt.

On occasion it might be desirable to nitrosate the alcohol after coupling the activated acylating agent to the alcohol. The activated acylating agent would be prepared from an acid containing a protected alcohol moiety. Preferred protecting groups for an alcohol moiety are silyl ethers, such as a trimethylsilyl ether, a tert-butyldimethylsilyl ether, or a tert-butyldiphenylsilyl ether. After formation of the ester, deprotection of the hydroxyl moiety (fluoride ion is the preferred method for removing silyl ether protecting groups) followed by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from –20° C. to room temperature, gives the compound of Formula VIIA. Alternately, nitrosation of the ester product may be accomplished by first converting the deprotected alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine in the presence of a halide source, such as carbon tetrabromide or N-iodosuccimide in an inert solvent, such as THF. Treatment of the bromide or iodide with silver nitrate in an inert solvent, such as acetonitrile, gives the compound of Formula VIIA. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile, gives the compound of Formula VIIA. Preferred coupling methods for the formation of esters from alcohols are those methods described herein (e.g. with the preformed acid chloride or anhydride or with the carboxylic acid and a dehydration agent, such as DCC or EDAC.HCl).

Scheme 7

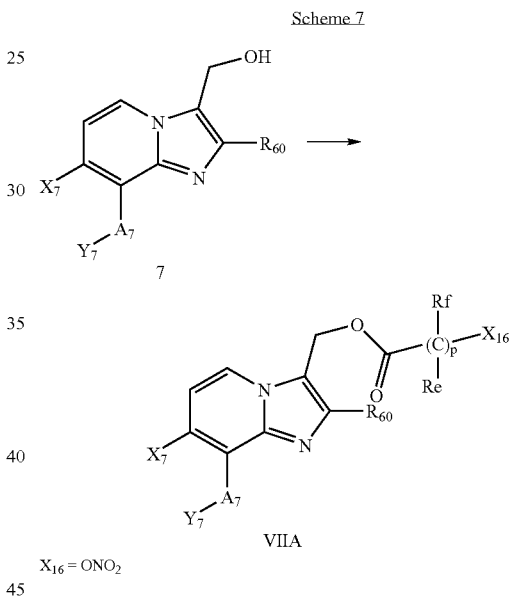

$X_{16} = ONO_2$

Alternately, nitrosation of the alcohol product in Formula 7 by reaction with a suitable nitrosating agent, such as nitric acid and acetic anhydride, nitric acid with sulfuric acid, or nitronium tetrafluoroborate, with or without a suitable inert solvent, such as ethyl acetate or chloroform, at a temperature ranging from –20° C. to room temperature, gives the compound of Formula VIIB as shown in Scheme 7A.

Scheme 7A

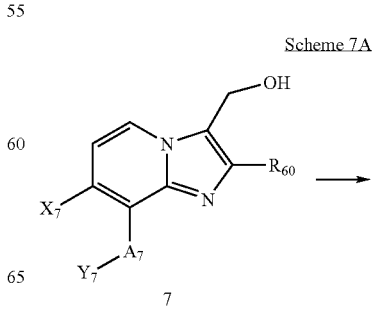

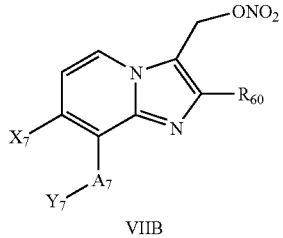

VIIB

The compounds of the invention include the proton pump inhibitors which have been nitrosated through one or more sites such as oxygen (hydroxyl condensation), sulfur (sulfhydryl condensation) and/or nitrogen. The nitrosated proton pump inhibitors of the invention donate, transfer or release a biologically active form of nitrogen monoxide (i.e., nitric oxide).

Nitrogen monoxide can exist in three forms: NO– (nitroxyl), NO• (uncharged nitric oxide) and NO+ (nitrosonium). NO• is a highly reactive short-lived species that is potentially toxic to cells. This is critical because the pharmacological efficacy of NO depends upon the form in which it is delivered. In contrast to the nitric oxide radical (NO•), nitrosonium (NO$^+$) does not react with $O_2$ or $O_2^-$ species, and functionalities capable of transferring and/or releasing NO$^+$ and NO– are also resistant to decomposition in the presence of many redox metals. Consequently, administration of charged NO equivalents (positive and/or negative) is a more effective means of delivering a biologically active NO to the desired site of action.

Compounds contemplated for use in the invention, e.g., proton pump inhibitors that are nitrosated, through one or more sites such as oxygen (hydroxyl condensation), sulfur (sulfhydryl condensation) and/or nitrogen, are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO•) and charged nitrogen monoxide species, preferably charged nitrogen monoxide species, such as nitrosonium ion (NO$^+$) and nitroxyl ion (NO–). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z, 3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3): 165–198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_mSNO$;

(ii) $ONS(C(R_e)(R_f))_mR_e$; or (iii) $H_2N$—$CH(CO_2H)$—$(CH_2)_m$—$C(O)NH$—$CH(CH_2SNO)$—$CO)NH$—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q'-, or —(C(R$_g$)(R$_h$))$_k$-T-Q' or R$_e$ and R$_f$ taken together are an oxo, a methanthial, a heterocyclic ring, a cycloalkyl group, an oxime, a hydrazone or a bridged cycloalkyl group; Q' is —NO or —NO$_2$; and T is independently a covalent bond, a carbonyl, an oxygen, —S(O)$_o$— or —N(R$_a$)R$_i$—, wherein o is an integer from 0 to 2, R$_a$ is a lone pair of electrons, a hydrogen or an alkyl group; R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —CH$_2$—C(T-Q')(R$_g$)(R$_h$), or —(N$_2$O$_2$—)$^-$.M$^+$, wherein M$^+$ is an organic or inorganic cation; with the proviso that when R$_i$ is —CH$_2$—C(T-Q')(R$_g$)(R$_h$) or —(N$_2$O$_2$—).M$^+$; then "-T-Q'" can be a hydrogen, an alkyl group, an alkoxyalkyl group, an aminoalkyl group, a hydroxy group or an aryl group; and R$_g$ and R$_h$ at each occurrence are independently R$_e$;

In cases where R$_e$ and R$_f$ are a heterocyclic ring or taken together R$_e$ and R$_f$ are a heterocyclic ring, then R$_i$ can be a substituent on any disubstituted nitrogen contained within the radical wherein R$_i$ is as defined herein.

Nitrosothiols can be prepared by various methods of synthesis. In general, the thiol precursor is prepared first, then converted to the S-nitrosothiol derivative by nitrosation of the thiol group with NaNO$_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—N— or ON—N— group. The compounds that include at least one ON—N— or ON—N— group are preferably ON—N— or ON—N-polypeptides (the term "polypeptide" includes proteins and polyamino acids that do not possess an ascertained biological function, and derivatives thereof); ON—N— or ON—N-amino acids (including natural and synthetic amino acids and their stereoisomers and racemic mixtures); ON—N— or ON—N-sugars; ON—N— or —ON—N— modified or unmodified oligonucleotides (comprising at least 5 nucleotides, preferably 5–200 nucleotides); ON—N— or ON—N— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one O$_2$N—O—, O$_2$N—N— or O$_2$N—S— group. Preferred among these compounds are O$_2$N—O—, O$_2$N—N— or O$_2$N—S— polypeptides (the term "polypeptide" includes proteins and also polyamino acids that do not possess an ascertained biological function, and derivatives thereof); O$_2$N—O—, O$_2$N—N— or O$_2$N—S— amino acids (including natural and synthetic amino acids and their stereoisomers and racemic mixtures); O$_2$N—O—, O$_2$N—N— or O$_2$N—S— sugars; O$_2$N—O—, O$_2$N—N— or O$_2$N—S— modified and unmodified oligonucleotides (comprising at least 5 nucleotides, preferably 5–200 nucleotides); O$_2$N—O—, O$_2$N—N— or O$_2$N—S— straight or branched, saturated or unsaturated, aliphatic or aromatic, substituted or unsubstituted hydrocarbons; and O$_2$N—O—, O$_2$N—N— or O$_2$N—S— heterocyclic compounds. Preferred examples of compounds comprising at least one O$_2$N—O—, O$_2$N—N— or O$_2$N—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: R$^{1''}$R$^{2''}$N—N(O—M$^+$)—NO, where R$^{1''}$ and R$^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M$^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

The invention is also based on the discovery that compounds and compositions of the invention may be used in conjunction with other therapeutic agents for co-therapies, partially or completely, in place of other therapeutic agents, such as, for example, NSAIDs, selective COX-2 inhibitors, H$_2$ receptor antagonists, antacids, bismuth-containing reagents, antibacterial compounds, *Helicobacter pylori* inhibitors, gastroprokinetic compounds and mixtures of two or more thereof. The therapeutic agent may optionally be nitrosated and/or nitrosylated.

Suitable NSAIDs, include, but are not limited to, acetaminophen, aspirin, diclofenac, ibuprofen, ketoprofen, naproxen, indomethacin, including but not limited to pro-drugs thereof, and the like. Suitable NSAIDs are described more fully in the literature, such as in Goodman and Gilman, The Pharmacological Basis of Therapeutics (9th Edition), McGraw-Hill, 1995, Pgs. 617–657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

Suitable COX-2 inhibitors, include, but are not limited to, NS-386, nimesulide, flosulide, celecoxib, rofecoxib, COX-189, etoracoxib, Bextra, Dynastat, Arcoxia, SC-57666, DuP 697, SC-58125, SC-58635, and the like, and mixtures of two or more thereof. Suitable COX-2 inhibitors are in U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, and 5,639,780 and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343; and in STN file registry and phar; the disclosures of each of which are incorporated by reference herein in their entirety, the disclosures of which are incorporated herein by reference in their entirety.

Suitable H$_2$ receptor anatgonists, include, but are not limited to, cimetidine, roxatidine, rantidine and the like. Suitable H$_2$ receptor antagonists are described more fully in the literature, such as in Goodman and Gilman, The Pharmacological Basis of Therapeutics (9th Edition), McGraw-Hill, 1995, Pgs. 901–915; the Merck Index on CD-ROM, 13$^{th}$ Edition; and in WO 00/28988 assigned to NitroMed Inc., the disclosures of which are incorporated herein by reference in their entirety.

Suitable antacids, include, but are not limited to, aluminum hydroxide, magnesium hydroxide, magnesium carbonate, calcium carbonate, alginic acid and co-dried gels, such as, for example, aluminum hydroxide-magnesium carbonate co-dried gel, and mixtures of two or more thereof.

Suitable bismuth-containing reagents are prepared by boiling the aqueous solution of the free base of the proton pump inhibitor with at least one bismuth-containing reagent, such as for example a bismuth salt, including, but not limited to, bismuth citrate, bismuth subcitrate, bismuth salicylate, bismuth subsalicylate, bismuth tartaric acid, bismuth nitrate, bismuth gallate, and mixtures of two or more thereof. Suitable bismuth containing reagents are described in U.S. Pat. No. 5,403,830 and in Ivanov et al, *J. Pharm. Pharmacol.*, 48:297–301 (1996), the disclosures of each of which are incorporated by reference herein in their entirety.

Suitable antibacterial compounds include, but are not limited to, any antibacterial compound that is known in the art, including, such as, for example, β-lactam antibiotics, such as, for example, amoxycillin, ampicillin, cephalothin, cefaclor, cefixime, penicillin, benzylpenicillin, clarithromycin, and the like; macrolide antibiotics, such as, for example, erythromycin, clarithromycin, and the like; tetracycline compounds, such as, for example, tetracycline, doxycycline, and the like; aminoglycoside compounds, such as, for example, gentamycin, kanamycin, amikacin, and the like; quinolone compounds, such as, for example, norfloxacin, ciprofloxin, enoxacin, and the like; metronidazole, nitrofurantoin, chloramphenicol, and the like, and mixtures of two or more thereof. Some antibacterial compounds are disclosed in U.S. Pat. Nos. 5,629,305 and 5,599,794, and in WO 01/54691, the disclosures of each of which are incorporated herein in their entirety.

Suitable gastroprokinetic compounds, include, but are not limited to, cisapride, mosapride, and mixtures of two or more thereof.

Another embodiment of the invention provides methods for preventing and/or treating gastrointestinal disorders by administering to the patient in need thereof a therapeutically effective amount of the compounds and/or compositions described herein. Such gastrointestinal disorders refer to any disease or disorder of the upper gastrointestinal tract (e.g., esophagus, the stomach, the duodenum, jejunum) including, for example, inflammatory bowel disease, Crohn's disease, gastritis, irritable bowel syndrome, constipation, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of at least one nitrosated proton pump inhibitor: In another embodiment, the patient can be administered a therapeutically effective amount of at least one nitrosated proton pump inhibitor, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated proton pump inhibitor, and, at least one therapeutic agent, including but not limited to, NSAIDs, selective COX-2 inhibitors, antacids, bismuth-containing reagents, antibacterial compounds, H$_2$ antagonists, *Helicobacter pylori* inhibitors, gastroprokinetic compounds, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods to improve the gastroprotective properties, anti-*Helicobacter* properties and antacid properties of proton pump inhibitors by administering to a patient in need thereof a therapeutically effective amount of the compounds and/or compositions described herein. For example, the patient can be administered a therapeutically effective amount of at least one nitrosated proton pump inhibitor. In another embodiment, the patient can be administered a therapeutically effective amount of at least one bismuth-complex of the nitrosated proton pump inhibitor. In yet another embodiment the patient can be administered at least one nitrosated proton pump inhibitor and at least one compound that donates, transfers or releases nitric oxide, or elevates levels of endogenous EDRF or nitric oxide, or is a substrate for nitric oxide synthase. In another embodiment, the patient can be administered a therapeutically effective amount of at least one bismuth-complex of the nitrosated proton pump inhibitor and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated proton pump inhibitor, and/or at least one bismuth-complex of the nitrosated proton pump inhibitor, and, at least one therapeutic agent, including but not limited to, NSAIDs, selective COX-2 inhibitors, H$_2$ receptor antagonists, antacids, bismuth-containing reagents, *Helicobacter pylori* inhibitors, gastroprokinetic compounds, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods for facilitating wound healing (such as, for example, ulcer healing, bone healing including osteoporosis) by administering to the patient in need thereof a therapeutically effective amount of the compounds and/or compositions described herein. Wound refers to, and includes, any lesion that is characterized by loss of tissue, and, includes, but is not limited to, ulcers, cuts, burns, bone fractures, orthopedic procedure, wound infliction, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of at least one nitrosated proton pump inhibitor. In another embodiment, the patient can be administered a therapeutically effective amount of at least one nitrosated proton pump inhibitor and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated proton pump inhibitor, and, at least one therapeutic agent, including but not limited to, NSAIDs, selective COX-2 inhibitors, antacids, bismuth-containing reagents, antibacterial compounds, $H_2$ antagonists, *Helicobacter pylori* inhibitors, gastroprokinetic compounds, and, optionally, at least one nitric oxide donor. The compounds can be administered separately or in the form of a composition.

Another aspect of the invention provides methods for decreasing and/or reversing gastrointestinal toxicity and facilitate ulcer healing resulting from the administration of nonsteroidal antiinflammatory drugs (NSAIDs), selective COX-2 inhibitors, and the like, by administering to a patient in need thereof a therapeutically effective amount of the compounds and/or compositions described herein. For example, the patient can be administered a therapeutically effective amount of least one nitrosated proton pump inhibitor. In another embodiment, the patient can be administered a therapeutically effective amount of at least one nitrosated proton pump inhibitor, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated proton pump inhibitor, and, at least one therapeutic agent, including but not limited to, NSAIDs, selective COX-2 inhibitors, antacids, bismuth-containing reagents, antibacterial compounds, $H_2$ antagonists, *Helicobacter pylori* inhibitors, gastroprokinetic compounds, and, optionally, at least one nitric oxide donor. The compounds can be administered separately or in the form of a composition.

Yet another embodiment of the invention provides methods for treating and/or preventing bacterial infections by administering to the patient in need thereof a therapeutically effective amount of the compounds and/or compositions described herein. In one embodiment of the invention bacterial infections, include, but are not limited *Helicobacter pylori* infections. For example, the patient can be administered a therapeutically effective amount of least one nitrosated proton pump inhibitor. In another embodiment, the patient can be administered a therapeutically effective amount of at least one nitrosated proton pump inhibitor, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated proton pump inhibitor, and, at least one therapeutic agent, including but not limited to, cyclooxygenase-2 (COX-2) inhibitors, NSAIDs, antacids, bismuth-containing reagents, antibacterial compounds, $H_2$ antagonists, *Helicobacter pylori* inhibitors, gastroprokinetic compounds, and, optionally, at least one compound that donates, transfers or releases nitric oxide, or elevates levels of endogenous EDRF or nitric oxide, or is a substrate for nitric oxide synthase. In yet another embodiment, the therapeutic agent may optionally be nitrosated and/or nitrosyalted. The compounds can be administered separately or in the form of a composition.

Yet another embodiment of the invention provides methods for treating and/or preventing viral infections by administering to the patient in need thereof a therapeutically effective amount of the compounds and/or compositions described herein. For example, the patient can be administered a therapeutically effective amount of least one nitrosated proton pump inhibitor. In another embodiment, the patient can be administered a therapeutically effective amount of at least one nitrosated proton pump inhibitor, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated proton pump inhibitor, and, at least one therapeutic agent, including but not limited to, cyclooxygenase-2 (COX-2) inhibitors, NSAIDs, antacids, bismuth-containing reagents, antibacterial compounds, $H_2$ antagonists, *Helicobacter pylori* inhibitors, gastroprokinetic compounds, and, optionally, at least one compound that donates, transfers or releases nitric oxide, or elevates levels of endogenous EDRF or nitric oxide, or is a substrate for nitric oxide synthase. The compounds can be administered separately or in the form of a composition.

When administered separately, the nitrosated proton pump inhibitor can be administered about the same time as part of the overall treatment regimen, i.e., as a combination therapy. "About the same time" includes administering the nitrosated proton pump inhibitor. simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one nitrosated proton pump inhibitor and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the nitrosated proton pump inhibitor.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

In a preferred embodiment, the acid susceptible nitrosated proton pump inhibitors are prepared as enteric coated layered pellets, a capsule or a multiple unit tableted dosage form as disclosed in for example, U.S. Pat. No. 6,365,184 and in WO 03/022249, WO 01/66088, WO 00/12064, WO 97/25064 and WO 96/24375; the disclosures of each of which are incorporated by reference herein in their entirety.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

The preferred methods of administration of the nitrosated proton pump inhibitors and compositions for the treatment of gastrointestinal disorders are orally, bucally or by inhalation. The preferred methods of administration for the treatment of inflammation and microbial infections are orally, bucally, topically, transdermally or by inhalation.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given nitrosated proton pump inhibitor of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the proton pump inhibitor. The usual daily doses of proton pump inhibitors are about 10 mg to about 400 mg per day and the doses of nitric oxide donors in the pharmaceutical composition can be in amounts of about 1 to about 500 mg/kg of body weight daily, preferably about 1 to about 50 mg/kg of body weight daily. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the novel nitrosated proton pump inhibitor, and one or more of the NO donors described herein. Associated with such kits can be additional therapeutic agents or compositions (e.g., NSAIDs, selective COX-2 inhibitors, antacids, bismuth-containing reagents, antibacterial compounds, $H_2$ antagonists, *Helicobacter pylori* inhibitors, gastroprokinetic compounds, and the like, and mixtures of two or more thereof), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the invention.

Example 1

2-(Nitrooxy)ethyl 2-(((3-Methyl-4-(2,2,2-trifluoroethoxy)-2-pyridyl)methyl)sulfinyl)benzimidazolecarboxylate 1a. 2-(Nitrooxy)ethan-1-ol A mixture of 2-bromoethanol (5.18 g, 41 mmol) and silver nitrate (21.25 g, 125 mmol) in acetonitrile (100 mL) was stirred at room temperature for 22 hours and then concentrated to dryness. The residue was taken up in diethylether (100 mL), treated with a saturated aqueous NaCl solution (100 mL), and stirred for 5 minutes. After filtration, the organic layer was separated, washed with water, dried over sodium sulfate, filtered, concentrated and dried under vacuum to give the title compound (3.12 g, 71% yield) as a colorless oil. $^1$H NMR (300 MHz, CDCl$_3$) δ 4.61–4.57 (m, 2H), 3.94–3.91 (m, 2H), 2.12 (br, 1H).

1b. 2-(Nitrooxy)ethyl Chlorooate

A solution of phosgene (1.9 M, 74 mL, 140 mmol) in toluene was added to the product of Example 1a (2.98 g, 27.8 mmol). The mixture was stirred at room temperature for 18 hours and the hydrogen chloride gas produced during the reaction was released through a bubbler. A continuous stream of nitrogen was introduced to the bottom of the solution to remove the unreacted phosgene, which was intercepted with aqueous NaOH for destruction. The phosgene-free mixture was concentrated by rotary evaporation and the last traces of toluene were removed by vacuum drying to give the title compound (4.32 g, 91% yield) as a yellow liquid. $^1$H NMR (300 MHz, CDCl$_3$) δ 4.75–4.72 (m, 2H), 4.59–4.55 (m, 2H).

1c. 2—(Nitrooxy)ethyl 2-(((3-methyl-4-(2,2,2-trifluoroethoxy)-2 pyridyl)methyl)sulfinyl)benzimidazolecarboxylate To a stirred solution of lansoprazole (1.69 g, 4.57 mmol) in THF (50 mL) at 0° C. was added sodium hydride (95%, 0.127 g, 5.02 mmol) in portions. After 10 minutes, the product of Example 1b (0.864 g, 5.48 mmol) was added dropwise. The mixture was stirred at 0–3° C. under a nitrogen atmosphere for 55 minutes, at which point the lansoprazole had been consumed as indicated by TLC. The mixture was taken up in ethyl acetate, washed with brine (3 times), dried over sodium sulfate, filtered through a pad of Celite, and concentrated by rotary evaporation. The crude product was purified by crystallization (3×) from 1:1 dichloromethane:hexanes to give the title compound (1.43 g, 62% yield) as a yellow solid. mp 117–120° C. $^1$H NMR (300 MHz, CDCl$_3$) δ 8.11 (d, J=5.6 Hz, 1H), 7.96 (d, J=7.4 Hz, 1H), 7.86 (d, J=7.3 Hz, 1H), 7.50–7.43 (m, 2H), 6.58 (d, J=5.6 Hz, 1H), 5.00–4.96 (m, 2H), 4.89–4.85 (m, 2H), 4.82 (d, J=12.4 Hz, 1H), 4.75 (d, J=12.4 Hz, 1H), 4.39 (q, $J_{F,H}$=7.8 Hz, 2H), 2.37 (s, 3H). LRMS (API-TIS) m/z 503.2 (MH$^+$).

Example 2

3-(Nitrooxy)propyl 2-(((3-methyl-4-(2,2,2-trifluoroethoxy)-2-pyridyl)methyl)sulfinyl)benzimidazolecarboxylate 2a. 3-(Nitrooxy)propan-1-ol A mixture of 3-bromopropanol (3.56 g, 25.6 mmol) and silver nitrate (13.1 g, 77 mmol) in acetonitrile (50 mL) was stirred at room temperature for 61 hours and then concentrated to dryness. The residue was suspended in diethylether (150 mL), a saturated aqueous NaCl solution (150 mL) was added, and the mixture was stirred for 10 minutes. After filtration, the organic layer was washed with water, dried over sodium sulfate, filtered, concentrated and dried under vacuum to give the title compound (2.05 g, 66% yield) as an oil. $^1$H NMR (300 MHz, CDCl$_3$) δ 4.61 (t, J=6.3 Hz, 2H), 3.75 (t, J=6.1 Hz, 2H), 2.81 (br, 1H), 2.02–1.93 (m, 2H).

2b. 3-(Nitrooxy)propyl Chlorooate

A solution of phosgene (1.9 M, 26 mL, 50 mmol) in toluene was added to the product of Example 2a (2.00 g, 16.5 mmol), and the resulting solution was stirred at room temperature for 24 hours. A continuous stream of nitrogen was introduced to the bottom of the reaction mixture to remove the unreacted phosgene, which was intercepted with aqueous NaOH for destruction. The phosgene-free mixture was concentrated by rotary evaporation and the last traces of toluene were removed by vacuum drying to give the title compound (2.20 g, 73% yield) as a liquid. $^1$H NMR (300 MHz, CDCl$_3$) δ 4.59 (t, J=6.2 Hz, 2H), 4.44 (t, J=6.1 Hz, 2H), 2.24–2.15 (m, 2H).

2c. 3-(Nitrooxy)propyl 2-(((3-methyl-4-(2,2,2-trifluoroethoxy)-2-pyridyl)methyl)sulfinyl)benzimidazolecarboxylate To a stirred solution of lansoprazole (2.58 g, 6.98 mmol) in THF (100 mL) at 0° C. was added sodium hydride (95%, 0.195 g, 7.7 mmol) in portions. After 15 minutes, the product of Example 2b (1.41 g, 7.68 mmol) was added dropwise. The mixture was stirred at 0–3° C. under a nitrogen atmosphere for 90 minutes, at which point the lansoprazole had been consumed as indicated by TLC. The mixture was diluted with ethyl acetate, washed with brine (3 times), dried over sodium sulfate, filtered through a pad of Celite, and concentrated by rotary evaporation. The crude product was purified by crystallization twice from 1:1 dichloromethane:hexanes to give the title compound (2.56 g, 71% yield) as a bright yellow solid. mp 101–102° C. $^1$H NMR (300 MHz, CDCl$_3$) δ 8.13 (d, J=5.6 Hz, 1H), 7.99 (d, J=7.4 Hz, 1H), 7.88 (d, J=7.2 Hz, 1H), 7.54–7.44 (m, 2H), 6.59 (d, J=5.6 Hz, 1H), 4.87–4.71 (m, 6H), 4.39 (q, $J_{F,H}$=7.9 Hz, 2H), 2.5–2.3 (m, 2H), 2.39 (s, 3H). LRMS (API-TIS) m/z 517.4 (MH$^+$).

Example 3

5-(Nitrooxy)pentyl 2-(((3-methyl-4-(2,2,2-trifluoroethoxy)-2-pyridyl)methyl)sulfinyl)benzimidazolecarboxylate 3a. 5-(Nitrooxy)pentan-1-ol A mixture of 5-bromo-1-pentanol (4.90 g, 29.3 mmol) and silver nitrate (14.9 g, 88 mmol) in acetonitrile (120 mL) was stirred at room temperature for 41 hours and then concentrated to dryness. The residue was suspended in diethylether (150 mL), a saturated aqueous NaCl solution (150 mL) was added, and the mixture was stirred for 10 minutes. After filtration, the organic layer was washed with brine, dried over sodium sulfate, filtered, concentrated and dried under vacuum to give the title compound (3.10 g, 71% yield) as a yellow oil. $^1$H NMR (300 MHz, CDCl$_3$) δ 4.47 (t, J=6.6 Hz, 2H), 3.65 (t, J=6.2 Hz, 2H), 2.07 br, 1H), 1.80–1.74 (m, 2H), 1.64–1.45 (m, 4H). $^{13}$C NMR (75 MHz, CDCl$_3$) δ 73.2, 62.2, 31.9, 26.4, 21.9.

3b. 5-(Nitrooxy)pentyl Chlorooate

A solution of phosgene (1.9 M, 25 mL, 48 mmol) in toluene was added to the product of Example 3a (2.08 g, 13.9 mmol). After the resulting solution was stirred at room temperature for 15 hours, the complete conversion of the starting alcohol was achieved as judged by proton NMR analysis of a tiny aliquot. A continuous stream of nitrogen was introduced to the bottom of the reaction mixture to remove the unreacted phosgene, which was intercepted with aqueous NaOH for destruction. The phosgene-free mixture was concentrated by rotary evaporation and the last traces of toluene were removed by vacuum drying to give the title compound (2.56 g, 87% yield) as a yellow liquid. $^1$H NMR (300 MHz, CDCl$_3$) δ 4.48 (t, J=6.5 Hz, 2H), 4.34 (t, J=6.4 Hz, 2H), 1.85–1.74 (m, 4H), 1.59–1.50 (m, 2H). $^{13}$C NMR (75 MHz, CDCl$_3$) δ 150.7, 72.7, 71.5, 27.8, 26.3, 22.0.

3c. 5-(Nitrooxy)pentyl 2-(((3-methyl-4-(2,2,2-trifluoroethoxy)-2-pyridyl)methyl)sulfinyl)benzimidazolecarboxylate To a stirred solution of lansoprazole (3.69 g, 10 mmol) in THF (100 mL) at 0° C. was added sodium hydride (95%, 0.278 g, 11 mmol) in portions. After 15 minutes, the product of Example 3b (2.54 g, 12 mmol) was added dropwise. The mixture was stirred at 0–3° C. under a nitrogen atmosphere for 3 hours, at which point the lansoprazole had been consumed as indicated by TLC. The mixture was diluted with ethyl acetate, washed with brine (3 times), dried over sodium sulfate, filtered through a pad of Celite, and concentrated by rotary evaporation. Initial attempts to crystallize the crude solid from dichloromethane/hexanes gave an oily gum (4.63 g). However, crystallization of this gum from 1:3 acetone/hexanes gave the title compound (4.41 g, 81%)

as off-white needles. mp 109–110° C. (acetone/hexanes). $^1$H NMR (300 MHz, CDCl$_3$) δ 8.09 (d, J=5.6 Hz, 1H), 7.94 (d, J=7.7 Hz, 1H), 7.85 (d, J=7.9 Hz, 1H), 7.50–7.39 (m, 2H), 6.57 (d, J=5.6 Hz, 1H), 4.83 (d, J=13.2 Hz, 1H), 4.71 (d, J=13.2 Hz, 1H), 4.60 (t, J=6.5 Hz, 2H), 4.49 (t, J=6.3 Hz, 2H), 4.36 (q, J$_{FH}$=7.8 Hz, 2H), 2.37 (s, 3H), 2.00–1.94 (m, 2H), 1.88–1.80 (m, 2H), 1.70–1.61 (m, 2H). LRMS (API-TIS) m/z 545.2 (MH$^+$).

Example 4

3-(nitrooxy)-2-((nitrooxy)methyl)propyl 2-(((3-methyl-4-(2,2,2-trifluoroethoxy)-2-pyridyl)methyl)sulfinyl)benzinmidazolecarboxylate 4a. 3-(Nitrooxy)-2-((nitrooxy)methyl)propan-1-ol Nitric acid (3.00 mL, 63 mmol) was added to acetic anhydride (9 mL) at 0° C. with stirring. After 15 minutes, a slurry of 2-(hydroxymethyl)-1,3-propanediol (3.00 g, 28.3 mmol) in THF (50 mL) was added and the stirring was continued for 20 minutes (the mixture became homogeneous during the reaction). The mixture was diluted with ethyl acetate, washed with 2M aqueous Na$_2$CO$_3$ three times, dried over Na$_2$SO$_4$, filtered, and concentrated by rotary evaporation. Chromatography (silica gel, eluting with 1:5 to 1:0 gradient of EtOAc:Hexanes) gave the title compound (the less polar component, a colorless liquid, 1.22 g, 22% yield), along with 2-((nitrooxy)methyl)propane-1,3-diol (the more polar component, a colorless liquid, 1.36 g, 32% yield). Data for the title compound: $^1$H NMR (300 MHz, CDCl$_3$) δ 4.66–4.54 (m, 4H), 3.80 (d, J=5.4 Hz, 2H), 2.49–2.40 (m, 1H), 2.07 (br, 1H). $^{13}$C NMR (75 MHz, CDCl$_3$) δ 69.9, 59.5, 37.7.

4b. 2-((Nitrooxy)methyl)propane-1,3-diol

This compound was isolated from the mixture obtained in Example 4a. $^1$H NMR (300 MHz, CDCl$_3$) δ 4.61 (d, J=6.5 Hz, 2H), 3.91–3.78 (m, 4H), 2.66 (br, 2H), 2.19–2.14 (m, 1H). $^{13}$C NMR (75 MHz, CDCl$_3$) δ 71.1, 61.8, 40.5.

4c. 3-(Nitrooxy)-2-((nitrooxy)methyl)propyl 2-(((3-methyl-4-(2,2,2-trifluoroethoxy)-2-pyridyl)methyl)sulfinyl)benzimidazolecarboxylate A solution of phosgene (1.9 M, 9.3 mL, 17.6 mmol) in toluene was added to the product of Example 4a (1.15 g, 5.85 mmol) in THF (10 mL). The resulting solution was stirred at room temperature for 15 hours, at which time only 26% of the starting alcohol had been converted to the corresponding chloroformate, as determine by NMR analysis of an aliquot. To complete the reaction, additional phosgene (1.9 M, 20 mL) was introduced, and the mixture was agitated for 41 hours. A continuous stream of nitrogen was introduced to the bottom of the reaction mixture to remove the unreacted phosgene, which was intercepted with aqueous NaOH for destruction. The phosgene-free mixture was concentrated by rotary evaporation at 75° C. to dryness. At the end of the concentration, the residue darkened rapidly, and was used immediately for the following reaction without characterization.

In a separate flask were charged with lansoprazole (1.48 g, 4.00 mmol) and THF (36 mL). The resulting solution was cooled to 0° C. with stirring before adding NaH (95%, 0.111 g, 4.4 mmol). After 2 minutes, the dark brown residue described above was added as a solution in THF (5 mL). The lansoprazole was completely consumed within 135 minutes as indicated by TLC. The reaction mixture was diluted with ethyl acetate, washed with aqueous NaCl (3×), dried over Na$_2$SO$_4$, filtered through Celite, and concentrated by rotary evaporation. The crude product was crystallized (5×) from 1:2 acetone:hexanes until TLC showed a single spot. The title compound (1.78 g, 75% yield based on lansoprazole) was obtained as bright yellow flakes. mp 96–97° C. (acetone/hexanes). $^1$H NMR (300 MHz, CDCl$_3$) δ 8.09 (d, J=5.6 Hz, 1H), 7.96 (d, J=7.8 Hz, 1H), 7.82 (d, J=7.8 Hz, 1H), 7.51–7.39 (m, 2H), 6.59 (d, J=5.6 Hz, 1H), 4.9–4.6 (m, 8H), 4.38 (q, J$_{F,H}$=7.9 Hz, 2H), 2.99 (m, 1H), 2.34 (s, 3H). LRMS (API-TIS) m/z 592.2 (MH$^+$).

Example 5

6-(Nitrooxy)hexyl 2-(((3-methyl-4-(2,2,2-trifluoroethoxy)-2-pyridyl)methyl)sulfinyl)benzimidazolecarboxylate 5a. 6-(Nitrooxy)hexan-1-ol This compound was prepared according to a literature method (Kawashima, Y.; Ikemoto, T.; Horiguchi, A.; Hayashi, M.; Matsumoto, K.; Kawarasaki, K.; Yamazaki, R.; Okuyama, S.; Hatayama, K. *J. Med. Chem.* 1993, 36, 815–819) as a colorless liquid (2.49 g, 57% yield). $^1$H NMR (300 MHz, CDCl$_3$) δ 4.47 (t, J=6.6 Hz, 2H), 3.60 (t, J=6.5 Hz, 2H), 3.07 (br, 1H), 1.77–1.72 (m, 2H), 1.60–1.38 (m, 6H). $^{13}$C NMR (75 MHz, CDCl$_3$) δ 73.2, 62.0, 32.0, 26.4, 25.2, 25.0.

5b. 6-(Nitrooxy)hexyl Chlorooate

A solution of phosgene (1.9 M, 19 mL, 36 mmol) in toluene was added to the product of Example 5a (1.91 g, 11.7 mmol). After the resulting solution was stirred at room temperature for 21 hours, the complete conversion of the starting alcohol was achieved as judged by proton NMR analysis of an aliquot. A continuous stream of nitrogen was introduced to the bottom of the reaction mixture to remove the unreacted phosgene, which was intercepted with aqueous NaOH for destruction. The phosgene-free mixture was concentrated by rotary evaporation and the last traces of toluene were removed by vacuum drying to furnish the title compound (2.51 g, 95% yield) as a slightly yellow liquid. $^1$H NMR (300 MHz, CDCl$_3$) δ 4.46 (t, J=6.5 Hz, 2H), 4.33 (t, J=6.5 Hz, 2H), 1.79–1.71 (m, 4H), 1.49–1.43 (m, 4H). $^3$C NMR (75 MHz, CDCl$_3$) δ 150.5, 73.0, 71.9, 28.0, 26.5, 25.12, 25.06.

5c. 6-(Nitrooxy)hexyl 2-(((3-methyl-4-(2,2,2-trifluoroethoxy)-2 pyridyl)methyl)sulfinyl)benzimidazolecarboxylate To a stirred solution of lansoprazole (2.95 g, 8.00 mmol) in THF (80 mL) at 0° C. was added sodium hydride (95%, 0.227 g, 9.00 mmol) in portions. After 5 minutes, the product of Example 5b (2.26 g, 10.0 mmol) in THF (10 mL) was added. The mixture was stirred at 0–3° C. under a nitrogen atmosphere for 3 hours, at which point the lansoprazole had been consumed as indicated by TLC. The mixture was diluted with ethyl acetate, washed with brine (3 times), dried over sodium sulfate, filtered, and concentrated by rotary evaporation. The residue was purified by stirring crystallization twice from 1:2 acetone:hexanes to give the title compound (3.98 g, 89%) as slightly yellow prisms. mp 83–85° C. (acetone/hexanes). $^1$H NMR (300 MHz, CDCl$_3$) δ 8.10 (d, J=5.6 Hz, 1H), 7.94 (m, 1H), 7.84 (m, 1H), 7.48–7.41 (m, 2H), 6.56 (d, J=5.6 Hz, 1H), 4.83 (d, J=13.1 Hz, 1H), 4.70 (d, J=13.1 Hz, 1H), 4.59 (t, J=6.6 Hz, 2H), 4.46 (t, J=6.5 Hz, 2H), 4.36 (q, J$_{F,H}$=7.9 Hz, 2H), 2.37 (s, 3H), 1.99–1.93 (m, 2H), 1.80–1.75 (m, 2H), 1.56–1.51 (m, 4H). LRMS (API-TIS) m/z 559.2 (MH$^+$).

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A compound of Formula (I), or a pharmaceutically acceptable salt thereof;

wherein the compound of Formula (I) is:

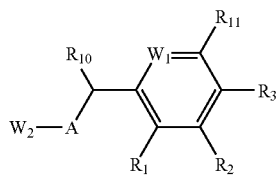

wherein
A is $S(O)_o$;
$W_1$ is —C—$NR_{87}R_{87}'$, —CH or nitrogen;
$W_2$ is:

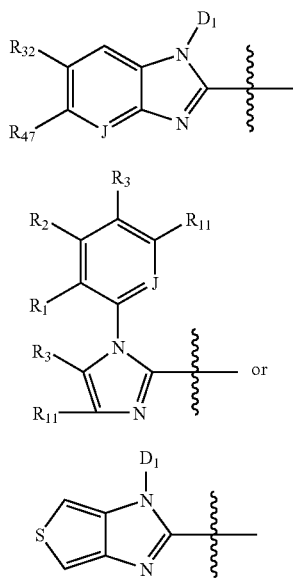

J is CH or nitrogen;
o is an integer from 0 to 2;
$R_1$ is a hydrogen, an alkoxy group, a lower alkyl group, or an alkylthio group;
$R_2$ is a hydrogen, a halogen, an alkoxy group, a lower alkyl group, an alkylthio group, a haloalkoxy group, an alkoxyalkyl group, —$NR_{87}R_{87}'$, —OX, or —SX; or $R_2$ and $R_3$ taken together with the carbon atoms to which they are attached form a cycloalkyl ring, an aryl group or a heterocyclic ring, and with the proviso that $R_2$ must be OX, or —SX in $W_2$;
$R_3$ and $R_{11}$ are each independently a hydrogen, an alkoxy group, a lower alkyl group, or an alkylthio group; or $R_3$ and $R_{11}$ taken together with the carbon chain to which they are attached form a cycloalkyl ring, an aryl group or a heterocyclic ring;
$R_{32}$ and $R_{47}$ are each independently a hydrogen, an alkyl group, a halo group, an alkoxy group, a haloalkyl group, a haloalkoxy group, a cyano group, an aryl group, a heterocyclic ring, —$NR_{87}R_{87}'$, —OX, or —$CO_2R_{12}$; or $R_{32}$ and $R_{47}$ taken together are:

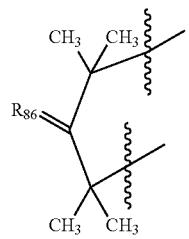

wherein
$R_{86}$ is oxygen or N═O—$R_{87}$;
$R_{87}$ and $R_{87}'$ are each independently hydrogen, a lower alkyl group, $D_1$ or X; or $R_{87}$ and $R_{87}'$ taken together with the nitrogen to which they are attached form a heterocyclic ring;
$R_{10}$ is a hydrogen; or $R_{10}$ and $R_1$ taken together with the carbon chain to which they are attached form a cycloalkyl ring;
$R_{12}$ is a lower alkyl group or X, with the proviso that Y in the definition of X must be oxygen or sulfur (—S—);
$D_1$ is:
(i) —$C(R_6R_6')$-T-C(O)—X;
(ii) —C(O)—X;
(iii) —$S(O)_2$—X;
(iv) —$C(R_6R_6')$-T-$S(O)_2$—X;
(v) —$C(R_6R_6')$—X; or
(vi) an inorganic cation;
$R_6$ and $R_6'$ are each independently a hydrogen, a lower alkyl group, an aryl group;
X is:
(1) —Y—$(CR_4R_4')_p$-T-$(CR_4R_4')_p$—$ONO_2$;

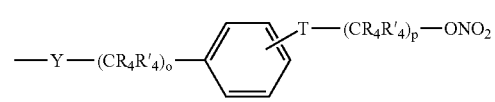

wherein T is ortho, meta or para;

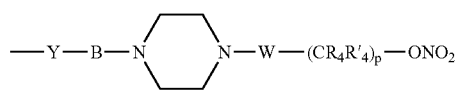

(4) —Y—$(CR_4R_4')_p$—V—B-T-$(CR_4R_4')_p$—$ONO_2$;
(5) —Y—$(CR_4R_4')_p$-T-C(O)—$(CR_4R_4')_o$—$(CH_2)$—$ONO_2$;
(6) —Y—$(CR_4R_4')_p$—C(Z)—$(CH_2)_q$-T-$(CR_4R_4')_q$—$(CH_2)$—$ONO_2$;
(7) —Y—$(CR_4R_4')_p$-T-$(CH_2)_q$—V—$(CR_4R_4')_q$—$(CH_2)$—$ONO_2$;

(8) —Y—(CR$_4$R$_4$')$_p$—V—(CH$_2$)$_q$—V—(CR$_4$R$_4$')$_q$—(CH$_2$)—ONO$_2$;
(9) —Y—(CR$_4$R$_4$')$_o$—(W)$_q$—(CR$_4$R$_4$')$_o$—(CH$_2$)—ONO$_2$;
(10) —NR$_j$—O—(CH$_2$)$_o$—V—(CR$_4$R$_4$')$_q$—(CH$_2$)—ONO$_2$;
(11) —NR$_j$—O—(CH$_2$)$_o$—(W)$_q$—(CR$_4$R$_4$')$_q$—(CH$_2$)—ONO$_2$;
(12) —O—NR$_j$—(CH$_2$)$_o$—(W)$_q$—(CR$_4$R$_4$')$_q$—(CH$_2$)—ONO$_2$;
(13) —Y—(CH$_2$)$_o$—(W)$_q$—(CH$_2$)$_o$—V—(CR$_4$R$_4$')$_o$-Q'-(CR$_4$R$_4$')$_o$—(CH$_2$)—ONO$_2$;
(14) —Y—(CR$_4$R$_4$')$_p$—V—(CH$_2$)$_o$—(W)$_q$—(CR$_4$R$_4$')$_q$—(CH$_2$)—ONO$_2$;
(15) —O—NR$_j$—(CH$_2$)$_o$—V—(CR$_4$R$_4$')$_q$—(CH$_2$)—ONO$_2$;
(16) —Y—(CR$_4$R$_4$')$_o$-Q'-(CR$_4$R$_4$')$_o$—V—(CR$_4$R$_4$')$_o$—(CH$_2$)—ONO$_2$;
(17) —Y—(CR$_4$R$_4$')$_o$-Q'-(CR$_4$R$_4$')$_o$—(W)$_q$—(CR$_4$R$_4$')$_o$—(CH$_2$)—ONO$_2$;
(18) —Y—(CR$_4$R$_4$')$_p$-T-(CR$_4$R$_4$')$_p$-Q'-(CR$_4$R$_4$')$_o$—(CH$_2$)—ONO$_2$;
(19) —Y—(CR$_4$R$_4$')$_q$—C(Z)-(CR$_4$R$_4$')$_o$—(CH$_2$)—ONO$_2$;
(20) —Y—(CR$_4$R$_4$')$_p$-Q'-(CR$_4$R$_4$')$_o$—(CH$_2$)—ONO$_2$;
(21) —Y—(CR$_4$R$_4$')$_q$—P(O)MM';
(22) —Y—(CR$_4$R$_4$')$_o$-Q'-(CR$_4$R$_4$')$_o$—(CH$_2$)—ONO$_2$;
(23) —Y—(CR$_4$R$_4$')$_o$-Q'-(CR$_4$R$_4$')$_o$-T-(CR$_4$R$_4$')$_o$—(CH$_2$)—ONO$_2$;
(24) —Y—(CR$_4$R$_4$')$_q$—(W)$_q$—(CR$_4$R$_4$')$_o$-Q'-(CR$_4$R$_4$')$_o$—(CH$_2$)—ONO$_2$;
(25) —Y—(CR$_4$R$_4$')$_q$—V—(CR$_4$R$_4$')$_o$-Q'-(CR$_4$R$_4$')$_o$—(CH$_2$)—ONO$_2$;
(26) —Y—(CR$_4$R$_4$')$_p$-(T)$_o$-(W)$_q$—(CR$_4$R$_4$')$_o$—(CH$_2$)—ONO$_2$;
(27) —Y—(CR$_4$R$_4$')$_p$—(W)$_q$-(T)$_o$-(CR$_4$R$_4$')$_o$—(CH$_2$)—ONO$_2$;
(28) —Y—(CR$_4$R$_4$')$_q$—C(Z)-V—(CR$_4$R$_4$')$_q$—(CH$_2$)—ONO$_2$;
(29) —Y—(CR$_4$R$_4$')$_o$—C(R$_4$)(ONO$_2$)—(CR$_4$R$_4$')$_q$-(T)$_o$-(W)$_q$-(T)$_o$-(CR$_4$R$_4$')$_o$—R$_5$;
(30) —Y—(CR$_4$R$_4$')$_o$—V—(CR$_4$R$_4$')$_o$-Q'-(CR$_4$R$_4$')$_o$—(CH$_2$)—ONO$_2$;
(31) —Y—(CR$_4$R$_4$')$_q$—C(Z)-Q'-(CR$_4$R$_4$')$_o$—(CH$_2$)—ONO$_2$;
(32) —Y—(CR$_4$R$_4$')$_p$—V—(CR$_4$R$_4$')$_p$—(CH$_2$)—ONO$_2$;
(33) —Y—(CR$_4$R$_4$')$_p$—V—(CH$_2$)$_q$-(T)$_o$-(CR$_4$R$_4$')$_q$—(CH$_2$)—ONO$_2$;
(34) —Y—(CR$_4$R$_4$')$_p$-(T)$_o$-Q'-(T)$_o$-(CR$_4$R$_4$')$_q$—(CH$_2$)—ONO$_2$;
(35) —Y—(CR$_4$R$_4$')$_q$—C(Z)—(CR$_4$R$_4$')$_q$—V—(CR$_4$R$_4$')$_o$-Q'-(CR$_4$R$_4$')$_o$—(CH$_2$)—ONO$_2$;
(36) —Y—(CR$_4$R$_4$')$_q$—C(Z)—(CR$_4$R$_4$')$_q$—(W)$_q$—(CR$_4$R$_4$')$_o$-Q'-(CR$_4$R$_4$')$_o$—(CH$_2$)—ONO$_2$;
(37) —NR$_j$—O—(CH$_2$)$_o$—V—(CR$_4$R$_4$')$_o$-Q'-(CH$_2$)—ONO$_2$;
(38) —NR$_j$—O—(CH$_2$)$_o$—(W)$_q$—(CR$_4$R$_4$')$_o$-Q'-(CH$_2$)—ONO$_2$;
(39) —O—NR$_j$—(CH$_2$)$_o$—(W)$_q$—(CR$_4$R$_4$')$_o$-Q'-(CH$_2$)—ONO$_2$;
(40) —O—NR$_j$—(CH$_2$)$_o$—V—(CR$_4$R$_4$')$_o$-Q'-(CH$_2$)—ONO$_2$;
(41) —NR$_j$—NR$_j$—(CR$_4$R$_4$')$_p$—(W)$_q$-(T)$_o$-(CR$_4$R$_4$')$_o$—(CH$_2$)—ONO$_2$; or
(42) —Y—(CR$_4$R$_4$')$_o$-Q'-(CR$_4$R$_4$')$_o$—ONO$_2$; or
(43) —Y—(CR$_4$R$_4$')$_o$—V—(CR$_4$R$_4$')$_o$-Q-(CR$_4$R$_4$')$_o$—ONO$_2$;

R$_4$ and R$_4$' at each occurrence are independently a hydrogen, lower alkyl group, —OH, —CH$_2$OH, —ONO$_2$, —NO$_2$ or —CH$_2$ONO$_2$; or R$_4$ and R$_4$' taken together with the carbon atom to which they are attached are a cycloalkyl group or a heterocyclic ring;
V is —C(O)-T-, -T-C(O)—, -T-C(O)-T or T-C(O)—C(O)-T;
W is a covalent bond or a carbonyl group;
T at each occurrence is independently an oxygen, (S(O)$_o$)$_o$ or NR$_j$;
R$_j$ is a hydrogen, an alkyl group, an aryl group, a heterocyclic ring, an alkylcarbonyl group, an alkylaryl group, an alkylsulfinyl group, an alkylsulfonyl group, an arylsulfinyl group, an arylsulfonyl group, a sulfonamido group, a N-alkylsulfonamido group, a N,N-diarylsulfonamido group, a N-arylsulfonamido group, a N-alkyl-N-arylsulfonamido group, a carboxamido group or a hydroxyl group;
p at each occurrence is independently an integer from 1 to 6;
q at each occurrence is independently an integer from 1 to 3;
Y is oxygen, sulfur (—S—), NR$_j$ or a covalent bond;
B is either phenyl or (CH$_2$)$_o$;
Q' is a cycloalkyl group, a heterocyclic ring or an aryl group;
Z is (═O), (═N—OR$_5$), (═N—NR$_5$R'$_5$) or (═CR$_5$R'$_5$);
M and M' are each independently —O$^-$ H$_3$N$^+$—(CR$_4$R'$_4$)$_q$—CH$_2$ONO$_2$ or -T-(CR$_4$R'$_4$)$_o$—CH$_2$ONO$_2$;
R$_5$ and R$_5$' at each occurrence are independently a hydrogen, a hydroxyl group, an alkyl group, an aryl group, an alkylsulfonyl group, an arylsulfonyl group, a carboxylic ester, an alkylcarbonyl group, an arylcarbonyl group, a carboxamido group, an alkoxyalkyl group, an alkoxyaryl group, a cycloalkyl group or a heterocyclic ring;
o is as defined herein; and
with the proviso that the compounds of Formula (I) must contain at least one nitrate group, and
with the further proviso for compounds of Formula (I):
when D$_1$ is —C(R$_6$R$_6$')-T-C(O)—X, T is oxygen, R$_6$ and R$_6$' are each independently a hydrogen or a lower alkyl group, X is Formula 1, R$_4$ and R$_4$' are both hydrogen, Y cannot be oxygen, NR$_j$ or a covalent bond when T is oxygen;
when D$_1$ is —C(R$_6$R$_6$')—X, R$_6$ and R$_6$' are each independently a hydrogen or a lower alkyl group, X is Formula 2, R$_4$ and R$_4$' are both hydrogen, Y cannot be a covalent bond or oxygen; and
with the proviso that the compounds of Formula (I) are not:

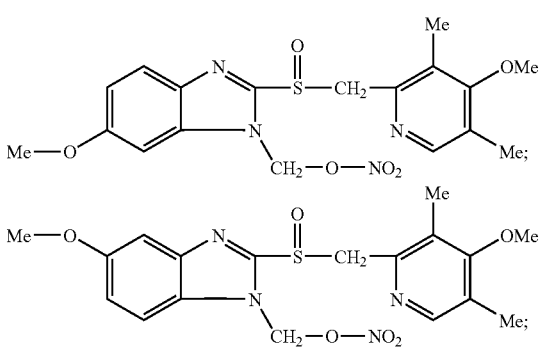

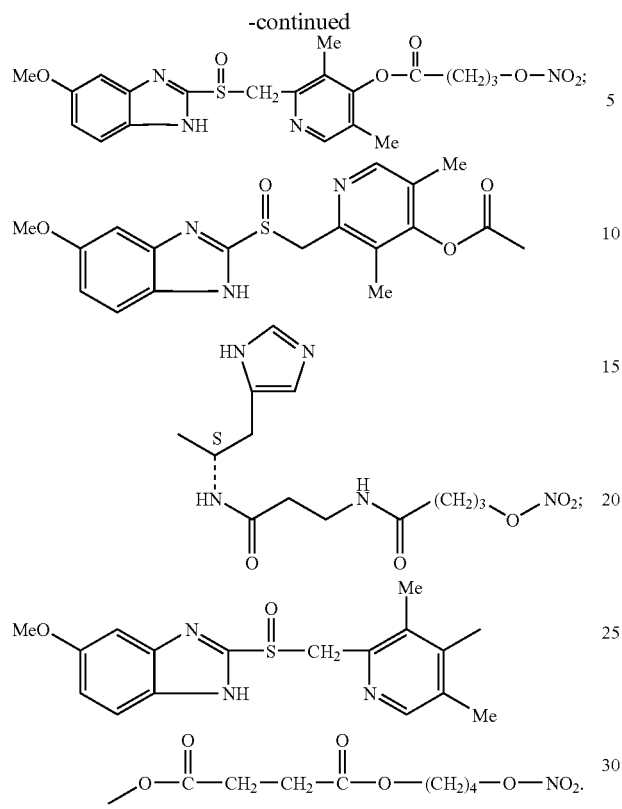
2. The compound of claim 1, wherein X is:
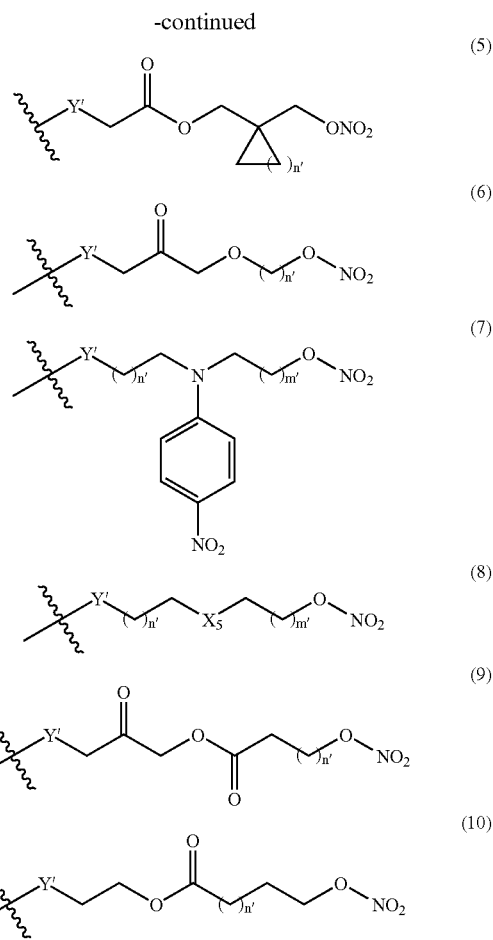
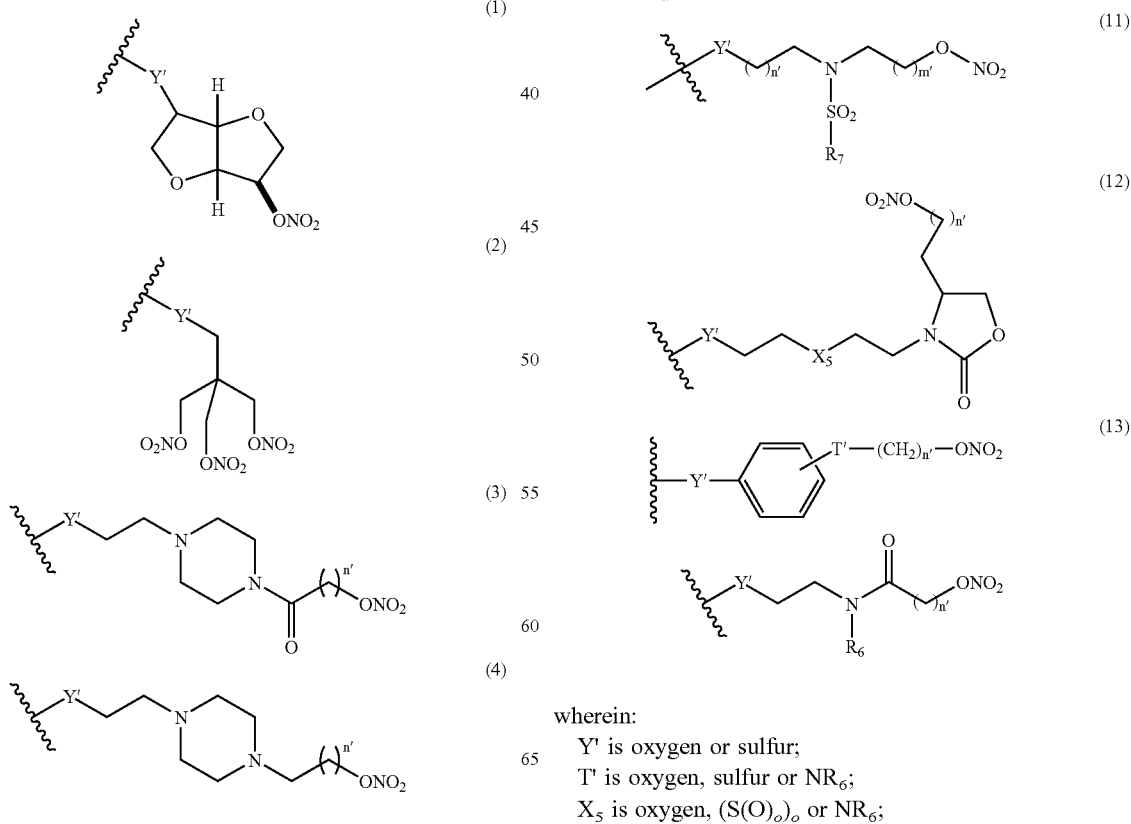
wherein:
Y' is oxygen or sulfur;
T' is oxygen, sulfur or NR$_6$;
X$_5$ is oxygen, (S(O)$_o$)$_o$ or NR$_6$;

$R_7$ is a lower alkyl group or an aryl group;

$R_8$ at each occurrence is independently is a hydrogen, a hydroxyl group, a lower alkyl group, an aryl group, —$NO_2$, —$CH_2$—$ONO_2$ or —$CH_2$—OH;

n' and m' are each independently an integer from 0 to 10;

$R_6$ and o are as defined herein; and with the proviso for Formula 8 for X, Y' and $X_5$ cannot be oxygen.

3. The compound of claim 1, wherein the compound of Formula (I) is a nitrosated imidazolo[5,4,-b]pyridine.

4. The compound of claim 3, wherein the nitrosated imidazolo[5,4,-b]pyridine is a nitrosated omeprazole, a nitrosated lansoprazole, a nitrosated pantoprazole, a nitrosated rabeprazole, a nitrosated leminoprazole, a nitrosated timoprazole, a nitrosated tenatoprazole, a nitrosated disulprazole, a nitrosated esomeprazole, a nitrosated 2-(2-benzimidazolyl)-pyridine, a nitrosated tricyclic imidazole, a nitrosated thienopydidine benzimidazole, a nitrosated fluoroalkoxy substituted benzimidazole, a nitrosated dialkoxy benzimidazole, a nitrosated N-substituted 2-(pyridylalkenesulfinyl) benzimidazole, a nitrosated cycloheptenepyridine, a nitrosated 5-pyrrolyl-2-pyridylmethylsulfinyl benzimidazole, a nitrosated alkylsulfinyl benzimidazole, a nitrosated fluoropyridylmethylsulfinyl benzimidazole, a nitrosated imidazo (4,5-b)pydridine, a nitrosated RO 18-5362, a nitrosated Hoe-731, a nitrosated TY 11345, a nitrosated IY 81149 or a nitrosated NC-1300 or a pharmaceutically acceptable salt thereof.

5. A composition comprising the compound of claim 1 and a pharmaceutically acceptable carrier.

6. A method for treating a gastrointestinal disorder, facilitating ulcer healing or decreasing the recurrence of an ulcer in a patient in need thereof comprising administering to the patient a therapeutically effective amount of the composition of claim 5.

7. The method of claim 6, wherein the gastrointestinal disorder is an inflammatory bowel disease, Crohn's disease, gastritis, irritable bowel syndrome, constipation, ulcerative colitis, a peptic ulcer, a stress ulcer, a bleeding ulcer, gastric hyperacidity, dyspepsia, gastroparesis, Zollinger-Ellison syndrome, gastroesophageal reflux disease, a bacterial infection, short-bowel (anastomosis) syndrome, or a hypersecretory state associated with systemic mastocytosis or basophilic leukemia and hyperhistaminemia.

8. A method for improving gastroprotective properties, the anti-*Helicobacter pylori* properties or antacid properties of a proton pump inhibitor comprising administering to a patient in need thereof a therapeutically effective amount of the composition of claim 5.

9. A method for decreasing gastrointestinal toxicity or facilitating ulcer healing resulting from administration of a nonsteroidal antiinflammatory drug and/or a selective COX-2 inhibitor to a patient comprising administering to a patient in need thereof a therapeutically effective amount of the composition of claim 5.

10. The composition of claim 5, further comprising at least one therapeutic agent.

11. The composition of claim 10, wherein the therapeutic agent is a nonsteroidal antiinflammatory compound, a selective cyclooxygenase-2 (COX-2) inhibitor, an antacid, a bismuth-containing reagent, an antibacterial compound, a $H_2$ antagonists, a gastroprokinetic compound, or a mixture of two or more thereof.

12. The composition of claim 11, wherein the nonsteroidal antiinflammatory compound is acetaminophen, aspirin, diclofenac, ibuprofen, ketoprofen, indomethacin or naproxen.

13. A method for treating a gastrointestinal disorder, facilitating ulcer healing or decreasing the recurrence of an ulcer in a patient in need thereof comprising administering to the patient a therapeutically effective amount of the composition of claim 10.

14. The method of claim 13, wherein the gastrointestinal disorder is an inflammatory bowel disease, Crohn's disease, gastritis, irritable bowel syndrome, constipation, ulcerative colitis, a peptic ulcer, a stress ulcer, a bleeding ulcer, gastric hyperacidity, dyspepsia, gastroparesis, Zollinger-Ellison syndrome, gastroesophageal reflux disease, a bacterial infection, short-bowel (anastomosis) syndrome, or a hypersecretory state associated with systemic mastocytosis or basophilic leukemia and hyperhistaminemia.

15. A method for improving gastroprotective properties, anti-*Helicobacter pylori* properties or antacid properties of a proton pump inhibitor comprising administering to a patient in need thereof a therapeutically effective amount of the composition of claim 10.

16. A method for decreasing gastrointestinal toxicity or facilitating ulcer healing resulting from administration of a nonsteroidal antiinflammatory drug and/or a selective COX-2 inhibitor to a patient comprising administering to a patient in need thereof a therapeutically effective amount of the composition of claim 10.

17. A kit comprising at least one compound of claim 1.

18. The kit of claim 17, further comprising at least one therapeutic agent.

19. The kit of claim 17, wherein the at least one therapeutic agent is in the form of a separate component in the kit.

20. A kit comprising the composition of claim 10.

21. A compound selected from the group consisting of:

2-(nitrooxy)ethyl 2-(((3-methyl-4-(2,2,2-trifluoroethoxy)-2-pyridyl)methyl)sulfinyl)benzimidazolecarboxylate;

3-(nitrooxy)propyl 2-(((3-methyl-4-(2,2,2-trifluoroethoxy)-2-pyridyl)methyl)sulfinyl)benzimidazolecarboxylate;

5-(nitrooxy)pentyl 2-(((3-methyl-4-(2,2,2-trifluoroethoxy)-2-pyridyl)methyl)sulfinyl)benzimidazolecarboxylate;

3-(nitrooxy)-2-((nitrooxy)methyl)propyl 2-(((3-methyl-4-(2,2,2-trifluoroethoxy)-2-pyridyl)methyl)sulfinyl)benzimidazolecarboxylate;

6-(nitrooxy)hexyl 2-(((3-methyl-4-(2,2,2-trifluoroethoxy)-2-pyridyl)methyl)sulfinyl)benzimidazolecarboxylate; or a pharmaceutically acceptable salt thereof.

22. A composition comprising at least one compound of claim 21 and a pharmaceutically acceptable carrier.

23. The composition of claim 22, further comprising at least one therapeutic agent.

24. A kit comprising at least one compound of claim 21.

* * * * *